United States Patent
Christadoss et al.

(10) Patent No.: US 8,530,245 B2
(45) Date of Patent: Sep. 10, 2013

(54) METHODS AND COMPOSITIONS RELATED TO ACETYLOCHOLINE RECEPTOR CONJUGATES

(75) Inventors: Premkumar Christadoss, League City, TX (US); Windy R. Allman, Rockville, MD (US)

(73) Assignee: The Board of Regents of the University of Texas System, Austin, TX (US)

( * ) Notice: Subject to any disclaimer, the term of this patent is extended or adjusted under 35 U.S.C. 154(b) by 105 days.

(21) Appl. No.: 13/056,399

(22) PCT Filed: Jul. 29, 2009

(86) PCT No.: PCT/US2009/052121
§ 371 (c)(1),
(2), (4) Date: Jun. 8, 2011

(87) PCT Pub. No.: WO2010/014723
PCT Pub. Date: Feb. 4, 2010

(65) Prior Publication Data
US 2011/0237688 A1 Sep. 29, 2011

Related U.S. Application Data

(60) Provisional application No. 61/084,504, filed on Jul. 29, 2008.

(51) Int. Cl.
*G01N 33/567* (2006.01)
(52) U.S. Cl.
USPC .......................................................... 436/501
(58) Field of Classification Search
None
See application file for complete search history.

(56) References Cited

U.S. PATENT DOCUMENTS

| | | | |
|---|---|---|---|
| 5,578,496 | A | 11/1996 | Atassi et al. |
| 2006/0286093 | A1 | 12/2006 | Gross et al. |
| 2007/0259421 | A1 | 11/2007 | D'Amour et al. |
| 2007/0269865 | A1 | 11/2007 | Fuchs et al. |

OTHER PUBLICATIONS

Accession No. AAD24503 (GI:4580859), Apr. 12, 1999.
Accession No. CA116184 (GI:55960912), Jan. 13, 2009.
Accession No. EAX11127 (GI:119631532), Feb. 4, 2010.
Accession No. NP_000742 (GI:4557461), Apr. 9, 2011.
Accession No. NP_001034612 (GI:87567783), Mar. 12, 2011.
Accession No. P02708 (GI:113071), May 31, 2011.
Accession No. P07510 (GI:126302510), Apr. 5, 2011.
Allman et al.,"Frequency of acetylcholine receptor specific B cells correlates with experimental myasthenia gravis severity," The Journal of Immunology, 1375:182, 2009.
Balass et al., "Identification of a hexapeptide that mimics a conformation-dependent binding site of acetylcholine receptor by use of a phage-epitope library," Proc. Natl. Acad. Sci. USA, 90(22): 10638-42, 1993.
Bartfeld and Fuchs, "Specific immunosuppression of experimental autoimmune myasthenia gravis by denatured acetylcholine receptor," Proc. Natl. Acad. Sci. USA, 75(8): 4006-4010, 1978.
Patrick and Lindstrom, "Autoimmune response to acetylcholine receptor," Science, 180:871-872, 1973.
PCT International Preliminary Report on Patentability issued in International Application No. PCT/US2009/052121, mailed Feb. 10, 2011.
PCT International Preliminary Report and Written Opinion issued in International Application No. PCT/US2009/052121, mailed Oct. 20, 2009.
Shenoy et al., "Suppression of experimental autoimmune myasthenia gravis by epitope-specific neonatal tolerance to synthetic region alpha 146-162 of acetylcholine receptor." Clin. Immunol. Immunopathol., 66(3): 230-238, 1993.
Silvy et al., "The differentiation of human memory B cells into specific antibody-secreting cells is CD40 independent," Eur J Immunol., 26(3):517-524, 1996.
Souroujon et al., "Regulation of experimental autoimmune myasthenia gravis by synthetic peptides of the acetylcholine receptor," Ann. NY Acad. Sci. 681:332-34, 1993.
Souroujon et al., "Modulation of anti-acetylcholine receptor antibody specificities and of experimental autoimmune myasthenia gravis by synthetic peptides," Immunol. Lett. 34(1):19-25, 1992.
Wikipedia Web Site, "B Cell." located at http://en.wikipedia.org/wiki/B-cell, downloaded Oct. 2009.
Wu et al., "Experimental autoimmune myasthenia gravis in the mouse," Curr. Protoc. Immunol., 15:Unit 15-18, 2001.

*Primary Examiner* — John Ulm

(57) ABSTRACT

Disclosed are methods, compositions, and diagnostic kits for detecting acetylcholine receptor (AchR) autoreactive immune cells in a subject. The methods comprise detecting the binding of AChR-conjugate to penpheral blood AChR-specific B cells for diagnosing autoimmune disorders, including Myasthenia gravis (MG), systemic lupus erythematous (SLE), and rheumatoid arthritis (RA). More specifically, the detection is achieved by using flow cytometric assay with Alexa-conjugated AchR.

17 Claims, 10 Drawing Sheets

SEQUENCE LISTING

```
<160> NUMBER OF SEQ ID NOS: 7

<210> SEQ ID NO 1
<211> LENGTH: 482
<212> TYPE: PRT
```

<213> ORGANISM: Homo sapiens

<400> SEQUENCE: 1

```
Met Glu Pro Trp Pro Leu Leu Leu Phe Ser Leu Cys Ser Ala Gly
1               5                   10                  15

Leu Val Leu Gly Ser Glu His Glu Thr Arg Leu Val Ala Lys Leu Phe
            20                  25                  30

Lys Asp Tyr Ser Ser Val Val Arg Pro Val Glu Asp His Arg Gln Val
            35                  40                  45

Val Glu Val Thr Val Gly Leu Gln Leu Ile Gln Leu Ile Asn Val Asp
        50                  55                  60

Glu Val Asn Gln Ile Val Thr Thr Asn Val Arg Leu Lys Gln Gly Asp
65                  70                  75                  80

Met Val Asp Leu Pro Arg Pro Ser Cys Val Thr Leu Gly Val Pro Leu
                85                  90                  95

Phe Ser His Leu Gln Asn Glu Gln Trp Val Asp Tyr Asn Leu Lys Trp
            100                 105                 110

Asn Pro Asp Asp Tyr Gly Gly Val Lys Lys Ile His Ile Pro Ser Glu
            115                 120                 125

Lys Ile Trp Arg Pro Asp Leu Val Leu Tyr Asn Asn Ala Asp Gly Asp
        130                 135                 140

Phe Ala Ile Val Lys Phe Thr Lys Val Leu Leu Gln Tyr Thr Gly His
145                 150                 155                 160

Ile Thr Trp Thr Pro Pro Ala Ile Phe Lys Ser Tyr Cys Glu Ile Ile
                165                 170                 175

Val Thr His Phe Pro Phe Asp Glu Gln Asn Cys Ser Met Lys Leu Gly
            180                 185                 190

Thr Trp Thr Tyr Asp Gly Ser Val Val Ala Ile Asn Pro Glu Ser Asp
            195                 200                 205

Gln Pro Asp Leu Ser Asn Phe Met Glu Ser Gly Glu Trp Val Ile Lys
        210                 215                 220

Glu Ser Arg Gly Trp Lys His Ser Val Thr Tyr Ser Cys Cys Pro Asp
225                 230                 235                 240

Thr Pro Tyr Leu Asp Ile Thr Tyr His Phe Val Met Gln Arg Leu Pro
                245                 250                 255

Leu Tyr Phe Ile Val Asn Val Ile Ile Pro Cys Leu Leu Phe Ser Phe
            260                 265                 270

Leu Thr Gly Leu Val Phe Tyr Leu Pro Thr Asp Ser Gly Glu Lys Met
            275                 280                 285

Thr Leu Ser Ile Ser Val Leu Leu Ser Leu Thr Val Phe Leu Leu Val
        290                 295                 300

Ile Val Glu Leu Ile Pro Ser Thr Ser Ser Ala Val Pro Leu Ile Gly
305                 310                 315                 320

Lys Tyr Met Leu Phe Thr Met Val Phe Val Ile Ala Ser Ile Ile Ile
                325                 330                 335

Thr Val Ile Val Ile Asn Thr His His Arg Ser Pro Ser Thr His Val
            340                 345                 350

Met Pro Asn Trp Val Arg Lys Val Phe Ile Asp Thr Ile Pro Asn Ile
            355                 360                 365

Met Phe Phe Ser Thr Met Lys Arg Pro Ser Arg Glu Lys Gln Asp Lys
        370                 375                 380

Lys Ile Phe Thr Glu Asp Ile Asp Ile Ser Asp Ile Ser Gly Lys Pro
385                 390                 395                 400

Gly Pro Pro Pro Met Gly Phe His Ser Pro Leu Ile Lys His Pro Glu
```

-continued

```
                    405                 410                 415
Val Lys Ser Ala Ile Glu Gly Ile Lys Tyr Ile Ala Glu Thr Met Lys
            420                 425                 430
Ser Asp Gln Glu Ser Asn Asn Ala Ala Ala Glu Trp Lys Tyr Val Ala
        435                 440                 445
Met Val Met Asp His Ile Leu Leu Gly Val Phe Met Leu Val Cys Ile
    450                 455                 460
Ile Gly Thr Leu Ala Val Phe Ala Gly Arg Leu Ile Glu Leu Asn Gln
465                 470                 475                 480
Gln Gly

<210> SEQ ID NO 2
<211> LENGTH: 482
<212> TYPE: PRT
<213> ORGANISM: Homo sapiens

<400> SEQUENCE: 2

Met Glu Pro Trp Pro Leu Leu Leu Leu Phe Ser Leu Cys Ser Ala Gly
1               5                   10                  15
Leu Val Leu Gly Ser Glu His Glu Thr Arg Leu Val Ala Lys Leu Phe
            20                  25                  30
Lys Asp Tyr Ser Ser Val Val Arg Pro Val Glu Asp His Arg Gln Val
        35                  40                  45
Val Glu Val Thr Val Gly Leu Gln Leu Ile Gln Leu Ile Asn Val Asp
    50                  55                  60
Glu Val Asn Gln Ile Val Thr Thr Asn Val Arg Leu Lys Gln Gly Asp
65                  70                  75                  80
Met Val Asp Leu Pro Arg Pro Ser Cys Val Thr Leu Gly Val Pro Leu
                85                  90                  95
Phe Ser His Leu Gln Asn Glu Gln Trp Val Asp Tyr Asn Leu Lys Trp
            100                 105                 110
Asn Pro Asp Asp Tyr Gly Gly Val Lys Lys Ile His Ile Pro Ser Glu
        115                 120                 125
Lys Ile Trp Arg Pro Asp Leu Val Leu Tyr Asn Asn Ala Asp Gly Asp
    130                 135                 140
Phe Ala Ile Val Lys Phe Thr Lys Val Leu Leu Gln Tyr Thr Gly His
145                 150                 155                 160
Ile Thr Trp Thr Pro Pro Ala Ile Phe Lys Ser Tyr Cys Glu Ile Ile
                165                 170                 175
Val Thr His Phe Pro Phe Asp Glu Gln Asn Cys Ser Met Lys Leu Gly
            180                 185                 190
Thr Trp Thr Tyr Asp Gly Ser Val Val Ala Ile Asn Pro Glu Ser Asp
        195                 200                 205
Gln Pro Asp Leu Ser Asn Phe Met Glu Ser Gly Glu Trp Val Ile Lys
    210                 215                 220
Glu Ser Arg Gly Trp Lys His Ser Val Thr Tyr Ser Cys Cys Pro Asp
225                 230                 235                 240
Thr Pro Tyr Leu Asp Ile Thr Tyr His Phe Val Met Gln Arg Leu Pro
                245                 250                 255
Leu Tyr Phe Ile Val Asn Val Ile Ile Pro Cys Leu Leu Phe Ser Phe
            260                 265                 270
Leu Thr Gly Leu Val Phe Tyr Leu Pro Thr Asp Ser Gly Glu Lys Met
        275                 280                 285
Thr Leu Ser Ile Ser Val Leu Leu Ser Leu Thr Val Phe Leu Leu Val
    290                 295                 300
```

```
Ile Val Glu Leu Ile Pro Ser Thr Ser Ser Ala Val Pro Leu Ile Gly
305                 310                 315                 320

Lys Tyr Met Leu Phe Thr Met Val Phe Val Ile Ala Ser Ile Ile Ile
                325                 330                 335

Thr Val Ile Val Ile Asn Thr His His Arg Ser Pro Ser Thr His Val
            340                 345                 350

Met Pro Asn Trp Val Arg Lys Val Phe Ile Asp Thr Ile Pro Asn Ile
        355                 360                 365

Met Phe Phe Ser Thr Met Lys Arg Pro Ser Arg Glu Lys Gln Asp Lys
    370                 375                 380

Lys Ile Phe Thr Glu Asp Ile Asp Ile Ser Asp Ile Ser Gly Lys Pro
385                 390                 395                 400

Gly Pro Pro Pro Met Gly Phe His Ser Pro Leu Ile Lys His Pro Glu
                405                 410                 415

Val Lys Ser Ala Ile Glu Gly Ile Lys Tyr Ile Ala Glu Thr Met Lys
                420                 425                 430

Ser Asp Gln Glu Ser Asn Asn Ala Ala Glu Trp Lys Tyr Val Ala
            435                 440                 445

Met Val Met Asp His Ile Leu Leu Gly Val Phe Met Leu Val Cys Ile
    450                 455                 460

Ile Gly Thr Leu Ala Val Phe Ala Gly Arg Leu Ile Glu Leu Asn Gln
465                 470                 475                 480

Gln Gly

<210> SEQ ID NO 3
<211> LENGTH: 482
<212> TYPE: PRT
<213> ORGANISM: Homo sapiens

<400> SEQUENCE: 3

Met Glu Pro Trp Pro Leu Leu Leu Leu Phe Ser Leu Cys Ser Ala Gly
1               5                   10                  15

Leu Val Leu Gly Ser Glu His Glu Thr Arg Leu Val Ala Lys Leu Phe
            20                  25                  30

Lys Asp Tyr Ser Ser Val Val Arg Pro Val Glu Asp His Arg Gln Val
        35                  40                  45

Val Glu Val Thr Val Gly Leu Gln Leu Ile Gln Leu Ile Asn Val Asp
    50                  55                  60

Glu Val Asn Gln Ile Val Thr Thr Asn Val Arg Leu Lys Gln Gly Asp
65                  70                  75                  80

Met Val Asp Leu Pro Arg Pro Ser Cys Val Thr Leu Gly Val Pro Leu
                85                  90                  95

Phe Ser His Leu Gln Asn Glu Gln Trp Val Asp Tyr Asn Leu Lys Trp
            100                 105                 110

Asn Pro Asp Asp Tyr Gly Gly Val Lys Lys Ile His Ile Pro Ser Glu
        115                 120                 125

Lys Ile Trp Arg Pro Asp Leu Val Leu Tyr Asn Asn Ala Asp Gly Asp
    130                 135                 140

Phe Ala Ile Val Lys Phe Thr Lys Val Leu Leu Gln Tyr Thr Gly His
145                 150                 155                 160

Ile Thr Trp Thr Pro Pro Ala Ile Phe Lys Ser Tyr Cys Glu Ile Ile
                165                 170                 175

Val Thr His Phe Pro Phe Asp Glu Gln Asn Cys Ser Met Lys Leu Gly
            180                 185                 190
```

```
Thr Trp Thr Tyr Asp Gly Ser Val Ala Ile Asn Pro Glu Ser Asp
            195                 200                 205
Gln Pro Asp Leu Ser Asn Phe Met Glu Ser Gly Glu Trp Val Ile Lys
210                 215                 220
Glu Ser Arg Gly Trp Lys His Ser Val Thr Tyr Ser Cys Cys Pro Asp
225                 230                 235                 240
Thr Pro Tyr Leu Asp Ile Thr Tyr His Phe Val Met Gln Arg Leu Pro
                245                 250                 255
Leu Tyr Phe Ile Val Asn Val Ile Pro Cys Leu Leu Phe Ser Phe
            260                 265                 270
Leu Thr Gly Leu Val Phe Tyr Leu Pro Thr Asp Ser Gly Glu Lys Met
            275                 280                 285
Thr Leu Ser Ile Ser Val Leu Leu Ser Leu Thr Val Phe Leu Leu Val
290                 295                 300
Ile Val Glu Leu Ile Pro Ser Thr Ser Ser Ala Val Pro Leu Ile Gly
305                 310                 315                 320
Lys Tyr Met Leu Phe Thr Met Val Phe Val Ile Ala Ser Ile Ile Ile
                325                 330                 335
Thr Val Ile Val Ile Asn Thr His His Arg Ser Pro Ser Thr His Val
            340                 345                 350
Met Pro Asn Trp Val Arg Lys Val Phe Ile Asp Thr Ile Pro Asn Ile
            355                 360                 365
Met Phe Phe Ser Thr Met Lys Arg Pro Ser Arg Glu Lys Gln Asp Lys
            370                 375                 380
Lys Ile Phe Thr Glu Asp Ile Asp Ile Ser Asp Ile Ser Gly Lys Pro
385                 390                 395                 400
Gly Pro Pro Pro Met Gly Phe His Ser Pro Leu Ile Lys His Pro Glu
                405                 410                 415
Val Lys Ser Ala Ile Glu Gly Ile Lys Tyr Ile Ala Glu Thr Met Lys
            420                 425                 430
Ser Asp Gln Glu Ser Asn Asn Ala Ala Ala Glu Trp Lys Tyr Val Ala
            435                 440                 445
Met Val Met Asp His Ile Leu Leu Gly Val Phe Met Leu Val Cys Ile
            450                 455                 460
Ile Gly Thr Leu Ala Val Phe Ala Gly Arg Leu Ile Glu Leu Asn Gln
465                 470                 475                 480
Gln Gly

<210> SEQ ID NO 4
<211> LENGTH: 493
<212> TYPE: PRT
<213> ORGANISM: Homo sapiens

<400> SEQUENCE: 4

Met Ala Arg Ala Pro Leu Gly Val Leu Leu Leu Leu Gly Leu Leu Gly
1               5                   10                  15
Arg Gly Val Gly Lys Asn Glu Glu Leu Arg Leu Tyr His His Leu Phe
                20                  25                  30
Asn Asn Tyr Asp Pro Gly Ser Arg Pro Val Arg Glu Pro Glu Asp Thr
            35                  40                  45
Val Thr Ile Ser Leu Lys Val Thr Leu Thr Asn Leu Ile Ser Leu Asn
        50                  55                  60
Glu Lys Glu Glu Thr Leu Thr Thr Ser Val Trp Ile Gly Ile Asp Trp
65                  70                  75                  80
Gln Asp Tyr Arg Leu Asn Tyr Ser Lys Asp Asp Phe Gly Gly Ile Glu
```

```
                    85                  90                  95
Thr Leu Arg Val Pro Ser Glu Leu Val Trp Leu Pro Glu Ile Val Leu
                100                 105                 110
Glu Asn Asn Ile Asp Gly Gln Phe Gly Val Ala Tyr Asp Ala Asn Val
                115                 120                 125
Leu Val Tyr Glu Gly Gly Ser Val Thr Trp Leu Pro Pro Ala Ile Tyr
                130                 135                 140
Arg Ser Val Cys Ala Val Glu Val Thr Tyr Phe Pro Phe Asp Trp Gln
145                 150                 155                 160
Asn Cys Ser Leu Ile Phe Arg Ser Gln Thr Tyr Asn Ala Glu Glu Val
                165                 170                 175
Glu Phe Thr Phe Ala Val Asp Asn Asp Gly Lys Thr Ile Asn Lys Ile
                180                 185                 190
Asp Ile Asp Thr Glu Ala Tyr Thr Glu Asn Gly Glu Trp Ala Ile Asp
                195                 200                 205
Phe Cys Pro Gly Val Ile Arg Arg His His Gly Gly Ala Thr Asp Gly
                210                 215                 220
Pro Gly Glu Thr Asp Val Ile Tyr Ser Leu Ile Ile Arg Arg Lys Pro
225                 230                 235                 240
Leu Phe Tyr Val Ile Asn Ile Ile Val Pro Cys Val Leu Ile Ser Gly
                245                 250                 255
Leu Val Leu Leu Ala Tyr Phe Leu Pro Ala Gln Ala Gly Gly Gln Lys
                260                 265                 270
Cys Thr Val Ser Ile Asn Val Leu Leu Ala Gln Thr Val Phe Leu Phe
                275                 280                 285
Leu Ile Ala Gln Lys Ile Pro Glu Thr Ser Leu Ser Val Pro Leu Leu
                290                 295                 300
Gly Arg Phe Leu Ile Phe Val Met Val Val Ala Thr Leu Ile Val Met
305                 310                 315                 320
Asn Cys Val Ile Val Leu Asn Val Ser Gln Arg Thr Pro Thr Thr His
                325                 330                 335
Ala Met Ser Pro Arg Leu Arg His Val Leu Leu Glu Leu Leu Pro Arg
                340                 345                 350
Leu Leu Gly Ser Pro Pro Pro Glu Ala Pro Arg Ala Ala Ser Pro
                355                 360                 365
Pro Arg Arg Ala Ser Ser Val Gly Leu Leu Leu Arg Ala Glu Glu Leu
                370                 375                 380
Ile Leu Lys Lys Pro Arg Ser Glu Leu Val Phe Glu Gly Gln Arg His
385                 390                 395                 400
Arg Gln Gly Thr Trp Thr Ala Ala Phe Cys Gln Ser Leu Gly Ala Ala
                405                 410                 415
Ala Pro Glu Val Arg Cys Cys Val Asp Ala Val Asn Phe Val Ala Glu
                420                 425                 430
Ser Thr Arg Asp Gln Glu Ala Thr Gly Glu Glu Val Ser Asp Trp Val
                435                 440                 445
Arg Met Gly Asn Ala Leu Asp Asn Ile Cys Phe Trp Ala Ala Leu Val
                450                 455                 460
Leu Phe Ser Val Gly Ser Ser Leu Ile Phe Leu Gly Ala Tyr Phe Asn
465                 470                 475                 480
Arg Val Pro Asp Leu Pro Tyr Ala Pro Cys Ile Gln Pro
                485                 490

<210> SEQ ID NO 5
<211> LENGTH: 502
```

<212> TYPE: PRT
<213> ORGANISM: Homo sapiens

<400> SEQUENCE: 5

Met Ala Arg Arg Cys Gly Pro Val Ala Leu Leu Leu Gly Phe Gly Leu
1               5                   10                  15

Leu Arg Leu Cys Ser Gly Val Trp Gly Thr Asp Thr Glu Glu Arg Leu
            20                  25                  30

Val Glu His Leu Leu Asp Pro Ser Arg Tyr Asn Lys Leu Ile Arg Pro
        35                  40                  45

Ala Thr Asn Gly Ser Glu Leu Val Thr Val Gln Leu Met Val Ser Leu
    50                  55                  60

Ala Gln Leu Ile Ser Val His Glu Arg Glu Gln Ile Met Thr Thr Asn
65                  70                  75                  80

Val Trp Leu Thr Gln Glu Trp Glu Asp Tyr Arg Leu Thr Trp Lys Pro
                85                  90                  95

Glu Glu Phe Asp Asn Met Lys Lys Val Arg Leu Pro Ser Lys His Ile
            100                 105                 110

Trp Leu Pro Asp Val Val Leu Tyr Asn Asn Ala Asp Gly Met Tyr Glu
        115                 120                 125

Val Ser Phe Tyr Ser Asn Ala Val Val Ser Tyr Asp Gly Ser Ile Phe
    130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Phe Arg Ser Trp
                165                 170                 175

Thr Tyr Asp Arg Thr Glu Ile Asp Leu Val Leu Lys Ser Glu Val Ala
            180                 185                 190

Ser Leu Asp Asp Phe Thr Pro Ser Gly Glu Trp Asp Ile Val Ala Leu
        195                 200                 205

Pro Gly Arg Arg Asn Glu Asn Pro Asp Asp Ser Thr Tyr Val Asp Ile
    210                 215                 220

Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Val Phe
                245                 250                 255

Tyr Leu Pro Ser Asp Cys Gly Glu Lys Met Thr Leu Cys Ile Ser Val
            260                 265                 270

Leu Leu Ala Leu Thr Val Phe Leu Leu Leu Ile Ser Lys Ile Val Pro
        275                 280                 285

Pro Thr Ser Leu Asp Val Pro Leu Val Gly Lys Tyr Leu Met Phe Thr
    290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Lys
                325                 330                 335

Val Val Phe Leu Glu Lys Leu Pro Ala Leu Leu Phe Met Gln Gln Pro
            340                 345                 350

Arg His His Cys Ala Arg Gln Arg Leu Arg Leu Arg Arg Arg Gln Arg
        355                 360                 365

Glu Arg Glu Gly Ala Gly Ala Leu Phe Phe Arg Glu Ala Pro Gly Ala
    370                 375                 380

Asp Ser Cys Thr Cys Phe Val Asn Arg Ala Ser Val Gln Gly Leu Ala
385                 390                 395                 400

```
Gly Ala Phe Gly Ala Glu Pro Ala Pro Val Ala Gly Pro Gly Arg Ser
                405                 410                 415

Gly Glu Pro Cys Gly Cys Gly Leu Arg Glu Ala Val Asp Gly Val Arg
            420                 425                 430

Phe Ile Ala Asp His Met Arg Ser Glu Asp Asp Gln Ser Val Ser
        435                 440                 445

Glu Asp Trp Lys Tyr Val Ala Met Val Ile Asp Arg Leu Phe Leu Trp
    450                 455                 460

Ile Phe Val Phe Val Cys Val Phe Gly Thr Ile Gly Met Phe Leu Gln
465                 470                 475                 480

Pro Leu Phe Gln Asn Tyr Thr Thr Thr Thr Phe Leu His Ser Asp His
                485                 490                 495

Ser Ala Pro Ser Ser Lys
                500

<210> SEQ ID NO 6
<211> LENGTH: 517
<212> TYPE: PRT
<213> ORGANISM: Homo sapiens

<400> SEQUENCE: 6

Met Glu Gly Pro Val Leu Thr Leu Gly Leu Leu Ala Ala Leu Ala Val
1               5                   10                  15

Cys Gly Ser Trp Gly Leu Asn Glu Glu Glu Arg Leu Ile Arg His Leu
            20                  25                  30

Phe Gln Glu Lys Gly Tyr Asn Lys Glu Leu Arg Pro Val Ala His Lys
        35                  40                  45

Glu Glu Ser Val Asp Val Ala Leu Ala Leu Thr Leu Ser Asn Leu Ile
    50                  55                  60

Ser Leu Lys Glu Val Glu Glu Thr Leu Thr Thr Asn Val Trp Ile Glu
65                  70                  75                  80

His Gly Trp Thr Asp Asn Arg Leu Lys Trp Asn Ala Glu Glu Phe Gly
                85                  90                  95

Asn Ile Ser Val Leu Arg Leu Pro Pro Asp Met Val Trp Leu Pro Glu
            100                 105                 110

Ile Val Leu Glu Asn Asn Asn Asp Gly Ser Phe Gln Ile Ser Tyr Ser
        115                 120                 125

Cys Asn Val Leu Val Tyr His Tyr Gly Phe Val Tyr Trp Leu Pro Pro
    130                 135                 140

Ala Ile Phe Arg Ser Ser Cys Pro Ile Ser Val Thr Tyr Phe Pro Phe
145                 150                 155                 160

Asp Trp Gln Asn Cys Ser Leu Lys Phe Ser Ser Leu Lys Tyr Thr Ala
                165                 170                 175

Lys Glu Ile Thr Leu Ser Leu Lys Gln Asp Ala Lys Glu Asn Arg Thr
            180                 185                 190

Tyr Pro Val Glu Trp Ile Ile Asp Pro Gly Phe Thr Glu Asn
        195                 200                 205

Gly Glu Trp Glu Ile Val His Arg Pro Ala Arg Val Asn Val Asp Pro
    210                 215                 220

Arg Ala Pro Leu Asp Ser Pro Ser Arg Gln Asp Ile Thr Phe Tyr Leu
225                 230                 235                 240

Ile Ile Arg Arg Lys Pro Leu Phe Tyr Ile Ile Asn Ile Leu Val Pro
                245                 250                 255

Cys Val Leu Ile Ser Phe Met Val Asn Leu Val Phe Tyr Leu Pro Ala
            260                 265                 270
```

-continued

Asp Ser Gly Glu Lys Thr Ser Val Ala Ile Ser Val Leu Leu Ala Gln
            275                 280                 285

Ser Val Phe Leu Leu Ile Ser Lys Arg Leu Pro Ala Thr Ser Met
    290                 295                 300

Ala Ile Pro Leu Ile Gly Lys Phe Leu Leu Phe Gly Met Val Leu Val
305                 310                 315                 320

Thr Met Val Val Ile Cys Val Ile Val Leu Asn Ile His Phe Arg
                325                 330                 335

Thr Pro Ser Thr His Val Leu Ser Glu Gly Val Lys Lys Leu Phe Leu
                340                 345                 350

Glu Thr Leu Pro Glu Leu Leu His Met Ser Arg Pro Ala Glu Asp Gly
            355                 360                 365

Pro Ser Pro Gly Ala Leu Val Arg Arg Ser Ser Ser Leu Gly Tyr Ile
    370                 375                 380

Ser Lys Ala Glu Glu Tyr Phe Leu Leu Lys Ser Arg Ser Asp Leu Met
385                 390                 395                 400

Phe Glu Lys Gln Ser Glu Arg His Gly Leu Ala Arg Arg Leu Thr Thr
                405                 410                 415

Ala Arg Arg Pro Pro Ala Ser Ser Glu Gln Ala Gln Gln Glu Leu Phe
            420                 425                 430

Asn Glu Leu Lys Pro Ala Val Asp Gly Ala Asn Phe Ile Val Asn His
    435                 440                 445

Met Arg Asp Gln Asn Asn Tyr Asn Glu Glu Lys Asp Ser Trp Asn Arg
450                 455                 460

Val Ala Arg Thr Val Asp Arg Leu Cys Leu Phe Val Val Thr Pro Val
465                 470                 475                 480

Met Val Val Gly Thr Ala Trp Ile Phe Leu Gln Gly Val Tyr Asn Gln
                485                 490                 495

Pro Pro Pro Gln Pro Phe Pro Gly Asp Pro Tyr Ser Tyr Asn Val Gln
            500                 505                 510

Asp Lys Arg Phe Ile
            515

<210> SEQ ID NO 7
<211> LENGTH: 517
<212> TYPE: PRT
<213> ORGANISM: Homo sapiens

<400> SEQUENCE: 7

Met His Gly Gly Gln Gly Pro Leu Leu Leu Leu Leu Leu Ala Val
1               5                   10                  15

Cys Leu Gly Ala Gln Gly Arg Asn Gln Glu Glu Arg Leu Leu Ala Asp
                20                  25                  30

Leu Met Gln Asn Tyr Asp Pro Asn Leu Arg Pro Ala Glu Arg Asp Ser
            35                  40                  45

Asp Val Val Asn Val Ser Leu Lys Leu Thr Leu Thr Asn Leu Ile Ser
        50                  55                  60

Leu Asn Glu Arg Glu Glu Ala Leu Thr Thr Asn Val Trp Ile Glu Met
65                  70                  75                  80

Gln Trp Cys Asp Tyr Arg Leu Arg Trp Asp Pro Arg Asp Tyr Glu Gly
                85                  90                  95

Leu Trp Val Leu Arg Val Pro Ser Thr Met Val Trp Arg Pro Asp Ile
            100                 105                 110

Val Leu Glu Asn Asn Val Asp Gly Val Phe Glu Val Ala Leu Tyr Cys
        115                 120                 125

-continued

```
Asn Val Leu Val Ser Pro Asp Gly Cys Ile Tyr Trp Leu Pro Pro Ala
130                 135                 140
Ile Phe Arg Ser Ala Cys Ser Ile Ser Val Thr Tyr Phe Pro Phe Asp
145                 150                 155                 160
Trp Gln Asn Cys Ser Leu Ile Phe Gln Ser Gln Thr Tyr Ser Thr Asn
                165                 170                 175
Glu Ile Asp Leu Gln Leu Ser Gln Glu Asp Gly Gln Thr Ile Glu Trp
            180                 185                 190
Ile Phe Ile Asp Pro Glu Ala Phe Thr Glu Asn Gly Glu Trp Ala Ile
        195                 200                 205
Gln His Arg Pro Ala Lys Met Leu Leu Asp Pro Ala Ala Pro Ala Gln
210                 215                 220
Glu Ala Gly His Gln Lys Val Val Phe Tyr Leu Leu Ile Gln Arg Lys
225                 230                 235                 240
Pro Leu Phe Tyr Val Ile Asn Ile Ile Ala Pro Cys Val Leu Ile Ser
                245                 250                 255
Ser Val Ala Ile Leu Ile His Phe Leu Pro Ala Lys Ala Gly Gly Gln
            260                 265                 270
Lys Cys Thr Val Ala Ile Asn Val Leu Leu Ala Gln Thr Val Phe Leu
        275                 280                 285
Phe Leu Val Ala Lys Lys Val Pro Glu Thr Ser Gln Ala Val Pro Leu
290                 295                 300
Ile Ser Lys Tyr Leu Thr Phe Leu Leu Val Val Thr Ile Leu Ile Val
305                 310                 315                 320
Val Asn Ala Val Val Val Leu Asn Val Ser Leu Arg Ser Pro His Thr
                325                 330                 335
His Ser Met Ala Arg Gly Val Arg Lys Val Phe Leu Arg Leu Leu Pro
            340                 345                 350
Gln Leu Leu Arg Met His Val Arg Pro Leu Ala Pro Ala Ala Val Gln
        355                 360                 365
Asp Thr Gln Ser Arg Leu Gln Asn Gly Ser Ser Gly Trp Ser Ile Thr
370                 375                 380
Thr Gly Glu Glu Val Ala Leu Cys Leu Pro Arg Ser Glu Leu Leu Phe
385                 390                 395                 400
Gln Gln Trp Gln Arg Gln Gly Leu Val Ala Ala Leu Glu Lys Leu
                405                 410                 415
Glu Lys Gly Pro Glu Leu Gly Leu Ser Gln Phe Cys Gly Ser Leu Lys
            420                 425                 430
Gln Ala Ala Pro Ala Ile Gln Ala Cys Val Glu Ala Cys Asn Leu Ile
        435                 440                 445
Ala Cys Ala Arg His Gln Gln Ser His Phe Asp Asn Gly Asn Glu Glu
450                 455                 460
Trp Phe Leu Val Gly Arg Val Leu Asp Arg Val Cys Phe Leu Ala Met
465                 470                 475                 480
Leu Ser Leu Phe Ile Cys Gly Thr Ala Gly Ile Phe Leu Met Ala His
                485                 490                 495
Tyr Asn Arg Val Pro Ala Leu Pro Phe Pro Gly Asp Pro Arg Pro Tyr
            500                 505                 510
Leu Pro Ser Pro Asp
515
```

METHODS AND COMPOSITIONS RELATED TO ACETYLOCHOLINE RECEPTOR CONJUGATES

The present application is a national phase application under 35 U.S.C. §371 of International Patent Application PCT Application No. PCT/US2009/052121, filed 29 Jul. 2009, which claims the benefit of U.S. Provisional Application No. 61/084,504, filed 29 Jul. 2008. The entire contents of these applications are incorporated herein by reference.

BACKGROUND OF THE INVENTION

I. Field of the Invention

Embodiments of this invention are directed generally to immunology and medicine. In certain embodiments the invention is directed to detection of autoreactive immune cell (B cell) that recognize the acetylcholine receptor.

II. Background

Myasthenia gravis (MG) is a human autoimmune disorder characterized by muscle weakness and fatigability. In this disease, antibodies against the acetylcholine receptor (AChR) bind to the receptor and destroy the receptor and thus interfere with the transmission of signals from nerve to muscle at the neuromuscular junction (Patrick and Lindstrom, 1973).

The acetylcholine receptor molecule is a transmembrane glycoprotein consisting of five subunits, two $\alpha$, one $\beta$, one $\delta$, with either an $\epsilon$ of $\gamma$ subunit, organized in a barrel-staves-like structure around a central cation channel (Karlin, 1980; Changeux et al., 1984). Noda et al. (1983) described the cloning and sequence analysis of human genomic DNA encoding the $\alpha$-subunit precursor of muscle acetylcholine receptor, and Schoepfer et al. (1988) reported the cloning of the $\alpha$-subunit cDNA from the human cell line TE671. Human muscle AChR $\alpha$-subunit exists in two forms, one of which has 25 additional amino acid residues, inserted between positions 58 and 59, that are coded by the 75 bp exon p3A (Beeson et al., 1990). The $\alpha$-subunit of AChR contains both the site for acetylcholine binding and is the immunodominant region for anti-AChR immune responses. However, antibodies have been detected against all subunits of AChR.

The autoimmune response in myasthenia gravis is directed mainly towards the extracellular domain of the AChR $\alpha$-subunit (amino acids 1-210), and within it, primarily towards the main immunogenic region (MIR) encompassing amino acids 61-76 (Tzartos and Lindstrom, 1980; Tzartos et al., 1987; Loutrari et al., 1992). Many antibodies to the MIR bind only to the native conformation of the $\alpha$ subunits because they bind to sequences that are adjacent only in the native structure.

MG is currently treated by acetylcholinesterase inhibitors and by non-specific immunosuppressive drugs that have deleterious side effects. It would be preferable to treat MG with a method that involves antigen-specific immunotherapy but leaves the overall immune response intact. One such strategy of specific therapy could involve the administration of derivatives of AChR that do not induce myasthenia but are capable of affecting the immunopathogenic antibodies. However, since the anti-AChR antibody repertoire in myasthenia gravis has been shown to be polyclonal and heterogeneous (Drachman, 1994), the regulation of the disease requires modulation of many antibody specificities.

Previous studies were directed towards modulating the anti-AChR response and EAMG by either derivatives of Torpedo AChR, e.g., the reduced and carboxymethylated derivative, RCM-AChR (Bartfeld and Fuchs, 1978), synthetic peptides corresponding to Torpedo acetylcholine receptor (Shenoy et al., 1993), specific regions of AChR (Shenoy et al., 1993; Souroujon et al., 1992; Souroujon et al., 1993), or mimotopes selected from an epitope library (Balass et al., 1993). The Torpedo RCM-AChR did not induce EAMG in rabbits and was effective in suppressing the disease. However, RCM-AChR did induce EAMG in rats. The experiments carried out with the synthetic peptides and mimotopes were only partially successful in neutralizing MG autoimmune response, probably due to the incorrect folding of the short peptides that were recognized by only a portion of the anti-AChR antibodies and ineffective tolerance to acetylcholine receptor specific B cells.

MG is currently diagnosed by testing for antibodies against AChR by radioimmunoassay wherein the antigen is crude AChR extracted from human muscle or TE671 cells. This test presents some drawbacks, namely the antigen is not readily available and, in addition, the antibody titers detected are not well correlated with disease severity.

Thus, additional methods and compositions that are both reliable and convenient diagnostic test is needed.

SUMMARY OF THE INVENTION

Myasthenia Gravis is a chronic autoimmune condition characterized by fluctuating voluntary muscle weakness. Antibodies to acetylcholine receptors (AChR) destroy AChR in the neuromuscular junctions leading to MG. Symptoms of MG include fatigue, muscle weakness, double vision, drooping eyelids, and difficulty chewing or swallowing and in severe disease paralysis and respiratory distress. Currently, diagnosis of MG involves a combination of clinical history, nerve stimulation tests, and blood test for serum antibodies against AChR. Although serum antibodies to AChR are diagnostic for MG, the antibody titer does not correlate with disease severity and around 15% of patients with MG do not have serum antibodies to AChR. Therefore, a better marker for disease state is required to evaluate the clinical effectiveness of specific drugs in MG. Also the current test for anti-AChR antibodies, either radioimmunoassay or ELISA takes two days and has to be performed in special Medical centers like Mayo Clinic. The inventors have developed a simple novel reagent and/or kit comprising AChR conjugates, such as an Alexa-AChR conjugate, for flowcytometry of patient blood. The methods described herein typically use no radioactivity, and can screen MG patient blood samples in little over an hour for increased frequency of AChR+ B cells. This test could be performed in any hospitals or institutions having a FACS machine or access to such a facility or service. Since anti-AChR antibodies are secreted versions of the membrane bound B cell receptor (BCR) in MG patients, the inventors use AChR conjugates, e.g., Alexa-fluor AChR conjugates, to identify pathogenic AChR-specific B cells in blood of MG patients.

The present invention provides methods for monitoring MG in a subject comprising the steps of determining the presence and/or number of AChR reactive B-cells in a sample from the subject, determining the levels in a control sample, and assessing MG status in the subject relative to the control. Furthermore, this invention also describes how one can isolate and assess the function and biology of specific autoreactive cells that bind AChR.

Certain aspects of the invention includes methods of evaluating a patient for or with Myasthenia Gravis comprising the steps of: (i) contacting a sample comprising B cells with an acetylcholine receptor (AChR) conjugate; (ii) determining a level of AChR binding B cells in a sample; and (iii) comparing the level of AChR reactive B-cells with a reference or standard. In certain aspects the sample is a blood sample. In a further aspect the AChR conjugate comprises a fluorophore, such as, but not limited to Alexa fluorophore (e.g., Alexa-488 or Alexa-647). In other aspects determining a level of AChR binding B cells is by flow cytometry.

In other aspects the method can further comprise contacting the sample with B cell marker binding agent, such as but not limited to an antibody that binds a cell surface molecule including, but not limited to IgG, CD19, CD21, CD45R, CD20, CD22, CD23, and/or CD81.

In still further aspects, the methods can further comprise administering a treatment for myasthenia gravis.

In yet a further aspect includes a reagent and/or device for evaluating a patient of myasthenia gravis comprising an AChR conjugate.

In certain aspects the invention is directed to an acetylcholine receptor conjugate comprising at least 3, 4, 5, 6, 7, 8, 9, 10, 11, 12, 13, 14, 15, 16, 17, 18, 19, 20, 30, 50, 100 or more consecutive amino acids, including all values and ranges there between of an AChR polypeptide coupled to a detectable moiety.

Also contemplated are kits for detecting acetylcholine receptor reactive B cells comprising an acetylcholine receptor conjugate.

Certain aspects are also directed to methods of evaluating a patient for or with an autoimmune condition comprising the steps of: (i) contacting a sample comprising B cells with a protein or peptide conjugate that specifically binds a B cell associated with the autoimmune condition; (ii) determining a level of conjugate binding B cells in a sample; and (iii) comparing the level of conjugate reactive B-cells with a reference or standard. In certain aspects the autoimmune condition is MG, SLE or rheumatoid arthritis.

As used herein, the term "B cell" refers to a cell produced in the bone marrow expressing membrane-bound antibody specific for an antigen, in this case AChR. Following interaction with the antigen it differentiates into a plasma cell which secretes antibodies specific for the antigen or into a memory B cell. "B cell" and "B lymphocyte" is used interchangeably.

As used herein, the term "antigen-specific B cell" refers to a B cell which expresses antibodies that are able to distinguish between the antigen of interest (e.g., AChR) and other antigens and which specifically bind to that antigen of interest with high or low affinity but which do not bind to other antigens.

A "positive B cell" means any B cell which is labeled with any one of the labeling compounds of the invention and which is selected or sorted or otherwise separated from a mixture of cells by a device capable of detecting said labeling compound. For example, a B cell which is positive for a labeling compound of the invention is a B cell which is labeled with a labeling compound and which is selected by the device capable of detecting the labeling compound.

As used herein, the term "B cell marker" refers to surface molecules on the B cells which are specific for particular B cells. B cell markers suitable for use in the present invention include, but are not limited to surface IgG, kappa and lambda chains, Ig-alpha (CD79alpha), Ig-beta (CD79beta), CD19, B220 (CD45R), CD20, CD21, CD22, CD23, CD27, or any other CD antigen specific for B cells.

The term "bind" or "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused," "associated," and "attached."

As used herein, the term "labeling compound" refers to a compound used to label the AChR polypeptides or one or more B cell markers of the invention either directly or indirectly through, for example, a covalent bond, a tag, antibody, dioxigenin, or biotin. Such labels suitable for use in the present invention are well known in the art and include, but are not limited to fluorescent materials (e.g., PerCP, Allophycocyanin (APC), texas red, rhodamine, Cy3, Cy5, Cy5.5, Cy7, Alexa Fluor Dyes, phycoerythrin (PE), green fluorescent protein (GFP), a tandem dye (e.g., PE-Cy5), fluorescein isothiocyanate (FITC)), magnetic beads, radiolabel (e.g., $^{131}$I-labeled antibody, $^{90}$Y (a pure beta emitter)-labeled antibody, $^{211}$At-labeled antibody), an enzyme, avidin or biotin, or any other tag or label known in the art useful for labeling AChR polypeptide and/or at least a second B cell marker.

The composition of the invention can be labeled prior to or after contacting a sample comprising a mixture of cells with an AChR polypeptide. The AChR polypeptide can be labeled with a labeling compound such as avidin or biotin, dioxigenin, flag tag or any other tag known in the art. A detectable moiety can then be bound to the AChR polypeptide through a covalent bond, a labeled streptavidin, anti-dioxigenin, anti-flag or any other anti-tag. The sample may also be contacted with a second composition comprising an antibody to one or more B cell marker. Detectable moieties include, but are not limited to fluorescent materials, magnetic particles or radiolabels.

In one embodiment, two or more samples may be taken from a subject. A first sample can be taken from the subject before treatment with a therapeutic agent, which for example, establishes a baseline to compare subsequent sample(s). A second sample can then be taken after treatment with the therapeutic agent to assess the effects of treatment.

In another embodiment, the test sample is from the subject who has or is suspected of having MG and the control sample is from a subject that does not have MG. In certain aspects, these methods and compositions are useful for determining B cell levels in any subject for whom the knowledge of the B cell levels in the subject would be helpful in treating or managing MG. Therefore, this method can be useful for monitoring or treating subjects having or suspected of having MG or monitoring a subject with MG. Thus, this method is useful for monitoring B cells associated with MG.

The present invention also provides kits and articles of manufacture for assaying AChR reactive B-cells levels in a subject. A kit may comprise AChR conjugate and one or more detectable moieties as well the reagents needed to express, purify, manipulate, and/or label an AChR polypeptide.

Other embodiments of this invention also include similar conjugation procedure to conjugate Alexa or other dyes with proteins or peptides that bind to B cells associated with other autoimmune diseases to detect frequency of antigen specific B cells in these diseases. Examples of autoimmune diseases and relevant proteins (autoantigens) involved in the development of these autoimmune diseases are given in Table 1. A conjugate of these autoantigens are contemplated for the assessment of these autoimmune disorders.

TABLE 1

Other autoimmune diseases and their autoantigen(s).

| Autoimmune Diseases | Autoantigens |
|---|---|
| Systemic lupus erythematous (SLE) | DNA, RNA, Smith (SM) antigen |

TABLE 1-continued

Other autoimmune diseases and their autoantigen(s).

| Autoimmune Diseases | Autoantigens |
|---|---|
| Hashimoto's thyroiditis | Thyroglobulin (Tg) |
| Uveitis | Interphotoreceptor retinoid binding protein (IRBP) |
| Rheumatoid arthritis (RA) | Type II collagen, rheumatoid factor |
| Type I diabetes (IDDM) | Islet b cell antigens, glutamic acid decarboxylase (GAD), and insulin |
| Graves' disease (Thyrotoxicosis) | Thyroid stimulatory hormone receptor (TSHR) |
| Goodpasture's syndrome | Type IV collagen |
| Pemphigus vulgaris | Desmoglein 2 |
| Pemphigoid | Epidermal basement membrane protein |
| Pernicious anemia | Intrinsic factor, gastric parietal cell antigen |
| Addison's disease | Adrenal gland antigen |
| Autoimmune haemolytic anemia | Erythrocyte membrane protein |
| Idiopathic thrombocytopenic purpura | Platelet membrane protein |
| Multiple sclerosis | Myelin basic protein (MBP). Myelin oligodendrocyte glycoprotein (MOG), proteolipid protein (PLP) |
| Primary bilary cirrhosis | Pyruvate dehydrogenase |
| Celiac disease | Gluten (gliadin) |
| Vasculitis | Neutrophil cytoplasmic antigen |
| Sjogren's syndrome | Ribonucleoprotein antigens (RO/SSA and La/SSB) |

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
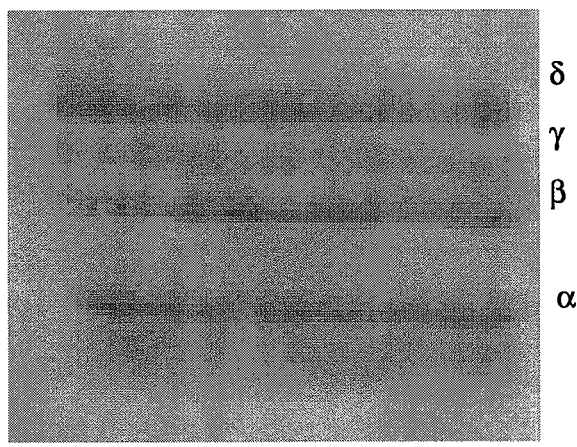
FIG. 1 A portion of affinity-purified AChR is run on an SDS-PAGE gel to test for high purity prior to labeling.

Patients with the neuromuscular disease Myasthenia Gravis (MG) are characterized by pathogenic autoantibodies directed towards AChR (Aharonov et al., 1975). The α-subunit of AChR is the immunodominant antigen, and within it especially the extracellular domain. Experimental autoimmune myasthenia gravis (EAMG) is an antibody-mediated autoimmune disease of the neuromuscular junction in which AChR is the major autoantigen and which serves as a model for MG.

Human muscle AChR α-subunit exists as two isoforms consisting of 437 and 462 amino acid residues (Beeson et al., 1990). The two isoforms are identical in their amino acid composition except for a sequence of 25 additional amino acid residues inserted after position 58 in the extracellular domain of the longer variant. These additional amino acids are encoded by the 75 bp exon p3A.

The AChR molecule in its native conformation structure, consisting of five subunits, two α, one β, one δ, with either an ε of γ subunits are included in present invention. However, this invention may be extended to fragments of AChR capable of binding and labeling a B-cell reactive with AChR as part of the present invention.

An "autoimmune disease," such as Myasthenia Gravis, is a disease or disorder arising from and directed against an individual's own tissues or organs, or a resulting condition there from. In many autoimmune disorders a number of clinical and laboratory markers may exist including, but not limited to production of autoantibodies. Without being limited to any one theory regarding autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, and/or direct chemokine release. Each of these pathways may participate to different degrees in the pathology of autoimmune diseases such as MG.

The term "determining" is intended to include any method for evaluating or measuring the amounts of a substance or cell type in a sample. Examples of comparative controls include, but are not limited to, sera from normal healthy patient samples or reference ranges derived the sampling an analysis of a number of subject known not to have MG.

I. Acetylcholine Receptor

An acetylcholine receptor (AChR) is an integral membrane protein that responds to the binding of the neurotransmitter acetylcholine. Human acetylcholine receptor consists of subunits, arising from five genes, CHRNA (e.g., Accession No. EAX11127 (GI:119631532); NP_001034612 (GI: 87567783); P02708 (GI:113071)), CHRNB2 (e.g., Accession No. CAI16184 (GI:55960912)), CHRND (e.g., Accession No. NP_000742 (GI:4557461)), CHRNE (e.g., Accession No. AAD24503 (GI:4580859)), and CHRNG (e.g., Accession No. P07510 (GI:126302510)), each of which is incorporated herein by reference as of the filing date of this application.

Molecular biology has shown that the nicotinic and muscarinic receptors belong to distinct protein superfamilies. The nAChRs are ligand-gated ion channels, and, like other members of the "cys-loop" ligand-gated ion channel superfamily, are composed of five protein subunits symmetrically arranged like staves around a barrel. The subunit composition is highly variable across different tissues. Each subunit contains four regions named M1, M2, M3, and M4, which span the membrane and consist of approximately 20 amino acids. The M2 region, which sits closest to the pore lumen, forms the pore lining. Binding of acetylcholine to the N termini of each of the two alpha subunits results in the 15° rotation of all M2 helices. The cytoplasm side of the nAChR receptor has rings of high negative charge that determine the specific cation specificity of the receptor and remove the hydration shell often formed by ions in aqueous solution.

AChR is found at the edges of junctional folds at the neuromuscular junction on the postsynaptic side, and is activated by acetylcholine release across the synapse. The diffusion of Na+ and K+ across the receptor causes depolarization, the end-plate potential, that opens voltage-gated sodium channels, which allows for firing of the action potential and potentially muscular contraction.

A. Conjugates

The invention provides a conjugate that contains a detectable moiety linked to an AChR polypeptide (e.g., affinity purified AchR). In certain aspects, the AChR polypeptide portion of the conjugate can have, for example, a length of at least, at most, or about 5, 10, 20, 30, 40, 50, 100, 150, 200, 250, 300, 400, or 450 consecutive amino acid residues, including all values and ranges there between, of for example SEQ ID NOs 1-3. It is understood that the term "AChR polypeptide portion of the conjugate" means the total number of residues in the AChR conjugate. An AChR polypeptide portion of the present invention may be prepared by purification methods, recombinant methods, and/or synthetic methods, all of which are known to one skilled in the art.

The AChR polypeptide portion according to the present invention may be prepared by recombinant methods. For example, a DNA nucleotide encoding the polypeptide is constructed by a conventional methods. The construction of the DNA nucleotide may be performed by PCR amplification using a suitable primer. Otherwise, the DNA nucleotide may be constructed by a standard method known to one skilled in the art, for example, by an automatic DNA synthesizer (available from Biosearch or Applied Biosystems). The DNA nucleotide constructed as described above is inserted into a vector containing at least one expression control sequence (e.g., promoter, enhancer, or the like) that is operatively linked to the DNA nucleotide to control the expression of the DNA nucleotide, thereby providing a recombinant expression vector, which, in turn, is used to transform a host cell. The resultant transformed cell can be cultured in a suitable medium and a condition to perform the expression of the DNA sequence. Then, a substantially pure peptide encoded by the DNA nucleotide is recovered from the culture. Such recovery may be carried out by a method generally known to one skilled in the art (e.g., chromatography). As used herein, the term "substantially pure peptide" means a peptide according to the present invention does not substantially comprise any other proteins derived from a host. References to the genetic engineering method for preparing the peptide according to the present invention include: Maniatis et al., 1982; Sambrook et al., $2^{nd}$ Ed. (1998) and $3^{rd}$ Ed. (2000); Gene Expression Technology, 1991; and Hitzeman et al., 1990.

Typical examples of synthetic methods include, but are not limited to, liquid or solid phase synthesis, fragment condensation, F-MOC or T-BOC chemistry ((Creighton, Proteins; Structures and Molecular Principles, 1983; Chemical Approaches to the Synthesis of Peptides and Proteins, 1997; A Practical Approach, 1989).

In a particular example AChR can be purified from a protein source such a cell line expressing a recombinant polypeptide or from Torpedo Californica electric organs (Aquatic Research Consultants, CA) according to published methods (Wu et al. 1997). AChR conjugates can be made by incubating AChR with detectable moiety containing a reactive moiety such as a succinimidyl ester moiety or other know reactive moiety. AChR polypeptides can be concentrated by, for example, centrifugation with centrifugal filters. AChR polypeptide can then be dialyzed and AChR concentration can be determined. AChR can then be contacted with a detectable moiety and/or a labeling reagent. Labeled AChR can then be further purified and concentration of labeled protein determined.

A number of peptide labeling methods are well known. (See Haugland, 2003; Brinkley, 1992; Garman, 1997; Means and Feeney, 1990; Glazer et al., 1975; Lundblad and Noyes, 1984; Pfleiderer, 1985; Wong, 1991; De Leon-Rodriguez et al., 2004; Lewis et al., 2001; Li et al., 2002; Mier et al., 2005).

B. Labeling and labels

In certain aspects an AChR polypeptide is conjugated to a detectable moiety by at least one covalent bond. In one aspect the covalent bond is a non-peptide bond. Typically AChR polypeptide is conjugated to the detectable moiety by way of chemical cross-linking, e.g., by using a heterobifunctional cross-linker A hetero-bifunctional crosslinker contains a functional group which can react with preferred first attachment sites, i.e. chemical groups of the AChR polypeptide and a further functional group which can react with a preferred second attachment site available for reaction with or the detectable moiety, vice versa with the first attachment site on the detectable moiety and the second attachment site on the AChR polypeptide. In certain aspects the chemical group for attachment can be synthesized in the detectable moiety itself, detectable moiety can have one or more attachment group(s). The first step of the procedure, typically called the derivatization, is the reaction of AChR polypeptide or the detectable moiety with the cross-linker. The product of this reaction is an activated AChR polypeptide or detectable moiety. In a second step, unreacted cross-linker is removed using usual methods such as column filtration, gel filtration, or dialysis.

Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA). The above mentioned cross-linkers all lead to formation of a thioether linkage. Other cross-linkers include for example SPDP and Sulfo-LC-SPDP (Pierce). The extent of derivatization with cross-linker can be influenced by varying conditions such as the concentration of each of the reaction partners, the excess of one reagent over the other, the pH, the temperature and the ionic strength. The degree of coupling, i.e. the amount of detectable moiety per AChR polypeptide, respectively, can be adjusted by varying the experimental conditions described above to match the requirements of the method of the invention. In a certain embodiment of the invention, the AChR polypeptide may be coupled, fused, or otherwise attached to a surface or substrate or particle.

Detectable moieties include fluorescent groups that are capable of absorbing radiation at one wavelength and emitting radiation at a longer wavelength, such as, for example, Alexa (e.g., Alexa-532, Alexa-488, Alexa-647, etc.), Hydroxycoumarin, Aminocoumarin, Methoxycoumarin, Coumarin, Cascade Blue, Lucifer Yellow, P-Phycoerythrin, R-Phycoerythrin, (PE), PE-Cy5 conjugates, PE-Cy7 conjugates, Red 613, Fluorescein, BODIPY-FL, BODIPY TR, BODIPY TMR, Cy3, TRITC, X-Rhodamine, Lissamine Rhodamine B, PerCP, Texas Red, Cy5, Cy7, Allophycocyanin (APC), TruRed, APC-Cy7 conjugates, Oregon Green, Tetramethylrhodamine, Dansyl, Dansyl aziridine, Indo-1, Fura-2, FM 1-43, DilC18(3), Carboxy-SNARF-1, NBD, Indo-1, Fluo-3, DCFH, DHR, SNARF, Monochlorobimane, Calcein, N-(7-nitrobenz-2-oxa-1,3-diazol-4-yl) amine (NBD), ananilinonapthalene, deproxyl, phthalamide, amino pH phthalamide, dimethylamino-naphthalenesulfonamide, probes comparable to Prodan, Lordan or Acrylodan and derivatives thereof. Coumarin fluorescent dyes include, for example, amino methylcoumarin, 7-diethylamino-3-(4'-(1-maleimidyl)phenyl)-4-methylcoumarin (CPM) and N-(2-(1-maleimidyl)ethyl)-7-diethylaminocoumarin-3-carboxamide (MDCC). Preferred fluorescent probes are sensitive to the polarity of the local environment and are available to those of skill in the art.

C. Detecting AChR Conjugate Binding

In addition to the above, the present invention also provides a kit for the evaluation, assessment, prognosis, and/or diagnosis of MG. The AChR polypeptide in the diagnosis kit may be prepared using the method as described above. In certain aspects, a labeled AChR will be provided. Additionally, in order to facilitate the identification, detection and determination of B cells according to the present invention the AChR polypeptide according to the present invention may be provided in a labeled form. In other words, the AChR polypeptide according to the present invention may be linked (covalently bonded or crosslinked) to a detectable label, i.e. provided as an AChR conjugate. Particular examples of the detectable label that may be used in the present invention include, in addition to those described above, color developing enzymes (e.g., peroxidase, alkaline phosphatase, etc.), radio isotopes (e.g., $^{125}I$, $^{32}P$, $^{35}S$, $^{131}I$, $^{124}I$, $^{18}F$, Tc99m etc.), chromophores, light emitting materials or fluorescent materials (e.g., FITC, RITC, etc.). In certain aspects the label is a fluorophore such as an Alexa fluorophore. Similarly, as the detectable label, it is possible to use an antibody epitope, substrate, cofactor, inhibitor or affinity ligand. Such labeling work may be performed during or after the preparation of the AChR polypeptide.

If a fluorescent material is used as the detectable material, evaluation of AChR reactive B cells may be performed by an immunofluorescence staining method. For example, after the AChR polypeptide according to the present invention, labeled with a fluorescent material, is allowed to react with a B cell, fluorescence caused by the AChR polypeptide may be detected by a number of devices. If any fluorescence is observed, the B cell is recognized as a AChR reactive B cell. Additionally, if an enzyme is used as the detectable label, absorbance is measured by the enzymatic color developing reaction of a substrate. On the other hand, if a radioactive material is used as the detectable label, radiation quantity is measured to detect an AChR reactive B cell, and thus to diagnose MG.

II. Polypeptides and Peptides

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to evaluate the immune status of a subject. The terms described above may be used interchangeably. A "modified protein" or "modified polypeptide" refers to a protein or polypeptide whose chemical structure, particularly its amino acid sequence, is altered with respect to the wild-type protein or polypeptide. In some embodiments, a modified protein or polypeptide has at least one modified activity or function (recognizing that proteins or polypeptides may have multiple activities or functions). It is specifically contemplated that a modified protein or polypeptide may be altered with respect to one activity or function yet retain a wild-type activity or function in other respects, such as binding affinity for AChR reactive B cells.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In certain aspects, the sequence of residues of the proteinaceous molecule may be interrupted by one or more non-amino molecule moieties. Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various AChR receptors are disclosed herein, and with a number of other AChR proteins and nucleic acids that can be found in the recognized computerized databases. One such database is the National Center for Biotechnology Information's GenBank and GenPept databases (on the World Wide Web at ncbi.nlm.nih.gov/). The coding regions for these genes may be amplified and/or expressed using the techniques disclosed herein or as would be know to those of ordinary skill in the art.

Amino acid sequence variants of AChR and other polypeptides of the invention can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, or more non-contiguous or contiguous amino acids of the polypeptide, as compared to wild-type.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

Proteins of the invention may be recombinant, or synthesized in vitro. Alternatively, a non-recombinant or recombinant protein may be isolated from bacteria or other expression host known in the art.

The term "functionally equivalent codon" is used herein to refer to codons that encode the same amino acid, such as the six codons for arginine or serine, and also refers to codons that encode biologically equivalent amino acids (see Table below).

TABLE 2

Codon Table

| Amino Acids | Codons |
| --- | --- |
| Alanine | Ala A GCA GCC GCG GCU |
| Cysteine | Cys C UGC UGU |
| Aspartic acid | Asp D GAC GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile I AUA AUC AUU |
| Lysine | Lys K AAA AAG |
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of or even an increase in the interactive binding capacity with AChR reactive B cells. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in sequences encoding AChR polypeptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example enzymes, substrates, cell surface receptors, DNA, antibodies, antigens, and the like. It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

A. Polypeptides and Polypeptide Production

The present invention describes polypeptides, peptides, and proteins for use in various embodiments of the present invention. For example, specific polypeptides are used to evaluate AChR autoreactivity. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

III. Nucleic Acids

In certain embodiments, the present invention concerns recombinant polynucleotides encoding the proteins, polypeptides, peptides of the invention. The nucleic acid sequences for AChR polypeptides are included, all of which are incorporated by reference, and can be used to prepare an AChR polypeptide conjugate.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene," "polynucleotide," or "nucleic acid" is used for to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more amino acids of a polypeptide of the invention. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode an AChR polypeptide. The term "recombinant" may be used in conjunction with a polypeptide or the name of a specific polypeptide, and this generally refers to a polypeptide produced from a nucleic acid molecule that has been manipulated in vitro or that is a replication product of such a molecule. In other embodiments, the invention concerns isolated nucleic acid segments and recombinant vectors incorporating nucleic acid sequences that encode an AChR polypeptide The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN®also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Kits

Another embodiment of the invention is a kit comprising a AChR conjugate. Optionally, the kit comprises reagents for detecting or assessing at least a second B cell marker.

The kit comprises at least one container and a label or package insert on or associated with the container. Suitable containers include, for example, bottles, vials, syringes, etc. The containers may be formed from a variety of materials such as glass or plastic. The container can have a sterile access port for reconstituting and/or extracting an agent (for example the container may be a vial having a stopper pierceable by a hypodermic injection needle). The label or package insert can indicate that the composition is used for assessing or evaluating MG. Additionally, the kit may further comprise a second container comprising a pharmaceutically-acceptable buffer, such as bacteriostatic water, phosphate-buffered saline, Ringer's solution and dextrose solution. It may further include other materials desirable from a commercial and user standpoint, including other buffers, diluents, filters, needles, and syringes.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Conjugation of Alexa Fluor 488 or 647 to AChR

AChR was purified from Torpedo Californica electric organs (Aqautic Research Consultants, CA) according to published methods (Wu et al., 1997)—AChR polypeptides include the polypeptides described in GenBank accession numbers AAR29363, AAR29362, AAR29361, AAA96705, AAA49276, AAA49275, AAA492774, including the corresponding human homologs, each of which is incorporated herein by reference in its entirety. Purified AChR protein was run in SDS page and fraction having 2 alpha and one of each beta, gamma, and delta subunits collected are shown in FIG. 1. Alexa Fluor-AChR conjugates were made by incubating AChR with Alexa Fluor 488 or 647 reactive dye (Invitrogen) which has a succinimidyl ester moiety that reacts efficiently with primary amines of proteins. AChR was concentrated by centrifugation with CentriconYM (10,000 molecular weight) centrifugal filters (Millipore, Mass.). AChR was then dialyzed in PBS using Spectra/Por dialysis tubing (12-14,000 molecular weight). AChR concentration was determined by the Bio-Rad Protein assay using BSA to generate a standard curve for known protein concentration. AChR was then diluted to 2 mg/ml using PBS. Fifty microliters of 1M sodium bicarbonate (pH 8.3) was added to 500 µl of AChR. Next, AChR was added to vial of Alexa fluor reactive dye provided in the Alexa Fluor Protein Labeling Kit. (Invitrogen) and incubated for 1 hr at room temperature (RT) with constant stirring. Labeled AChR was purified according to manufacturers instructions. Concentration of labeled protein was determined as described previously.

Example 2

Testing the Frequency of AChR Specific B Cells in Experimental Autoimmune Myasthenia Gravis To identify AChR-specific B cells, C57BL6 mice (Jackson Lab) were immunized with AChR to induce experimental autoimmune myasthenia gravis (EAMG) (Wu et al., 1997). Mice were sacrificed four weeks post-boost immunization and spleen cells were labeled with APC-anti-CD19, PE-anti-CD21/35, and Alexa 488-AChR. First lymphocytes were gated on single cells in suspension (FSC-A vs SSC-A, SSC-H vs SSC-W, and FSC-H vs FSC-W). Then cells were gated on B cells (APC-CD19) and analyzed for binding of PE-CD 21 (a mature B cell marker) and Alexa Flour 488 (FITC-like)-AChR. Mice immunized with AChR in complete Freund's adjuvant (CFA) had more than double the amount of mature AChR+ B cells (CD19+CD21+AChR+) than unimmunized naïve mice or CFA immunized mice. AChR in CFA immunized mice also had increased frequencies (mean 8.1%) of AChR+ B cells in the lymph node compared to naïve mice (3.8%). Also AChR+ (APC like Alex 647-AChR) binding B cells are consistently elevated weeks post immunization and the size of a majority of these cells are large (FSC-A), indicating that these cells are activated.

Alexa-AChR binding B cells were depleted and those B cell which are not bound to Alexa-AChR were tested for AChR specific B cell proliferation. Those B cells which did not bind to Alexa-AChR failed to induce AChR specific B cell proliferation.

These results indicate that it is possible to identify the presence of AChR-specific B cells in lymphocyte populations in vivo in EAMG mice. Now we can directly evaluate AChR-specific B cell activation, migration, survival and function in mice with MG. The Torpedo AChR has around 90% sequence homology with human AChR and human MG patients antibodies significantly cross react with Torpedo AChR. The following protocol can be used to test the frequency of Alexa-AChR specific B cells in MG patients.

Collection of Blood and Identification of AChR Binding B Cell Subsets:

1. Collect blood in K2EDTA 10 ml BD Vacutainer Tubes (BD-366643, BD Biosciences). Collect 3 tubes per patient.
2. Be sure to invert tube several times after blood has been collected.
3. Centrifuge blood tubes for 15 min at 500 g at room temperature (RT).
4. Remove plasma.
5. Transfer plasma free blood to 50 ml conical tube and add equal volume of RT PBS and mix well.
6. Layer blood over equal volume of Histopaque 1077 (10771-100 ml, Sigma-Aldrich).
7. Centrifuge without break at 800 g for 20 min at RT.
8. Remove lymphocyte layer and place in 15 ml conical tube. Wash with 10 ml RT PBS. Centrifuge at 300 g for 8 min at RT.
9. Repeat wash.
10. Resuspend cells in FACS Buffer (PBS, 2% FBS, 0.1% sodium azide) at $2 \times 10^7$ cells/ml.
11. Block cells by incubating with human IgG (1 µg/$10^6$ cells) for 20 min on ice. (I-4506, Sigma Aldrich).
12. Aliquot 100 µl of cells into 5 ml polystyrene round bottom tubes. Add 100 of fluorescent antibody (CD19, CD21) or fluorescent Alexa-AChR diluted in FACS Buffer (1 µg/$10^6$ cells).

Table 3 provides the antibody for staining to test the frequency of AChR specific B cells which are naïve/activated, memory, or plasma cells.

TABLE 3

|  | Naïve/Activated | Memory | Plasma |
|---|---|---|---|
| APC | AChR | AChR | AChR |
| FITC | CD27 | CD27 | IgG |
| PE | CD43 | CD138 | CD27 |
| PE-CY7 | CD19 | CD19 | CD38 |

Steps include:
1. Incubate with the above antibodies for 45 min at 4 degree C. in dark.
2. Add 2 ml of RT BD Pharm Lyse Buffer (555899), mix well, and incubate for 15 min at RT in dark.
3. Centrifuge for 5 min at 200 g. Discard Buffer.
4. Add 2 ml wash buffer, vortex, and centrifuge for 5 min at 200 g.

5. Repeat wash.
6. Resuspend 300 µl of 2% formaldehyde and store at 4° C.
7. Analyze using BD FACS-Canto.

The methods and compositions represented by these example can be used as follows: (1) For testing the frequency acetylcholine receptor specific B cells using Alexa-AChR conjugate for myasthenia gravis (MG) diagnosis, including those MG patients who are not diagnosed with the conventional sera anti-AChR antibody assay by RIA or ELISA. The Alexa-AChR conjugate could be further used as a rapid biomarker for disease activity and testing the frequency of pathogenic B cell population during treatment of specific drugs in MG patients. (2) Flow cytometry using Alexa-AChR will provide more information about the type of cells producing anti-AChR antibodies, such as antibody class, frequency of these specific B cells, and type of B cells. Anti-AChR antibody secreting B cells ($CD38^{hi}CD20^{-}CD27^{hi}CD21^{lo}$), naive B cells ($CD19+ CD27^{-}CD21^{hi}CD38^{lo}$), and memory B cells ($CD19+CD38^{+}CD138+CD27^{+}$) and possibly plasma cells can be detected. (3) Conjugation of human AChR or human AChR subunits (alpha, beta, epsilon, delta) or its extra cellular domain with Alexa to test the frequency of human AChR or its subunit specific B cells in MG and correlating with disease activity. (4) Use of Alexa-AChR or subunits of various species to test the frequency of AChR or subunit specific B cells during various stages of development in various animal models of MG and MG.

Figure 2:
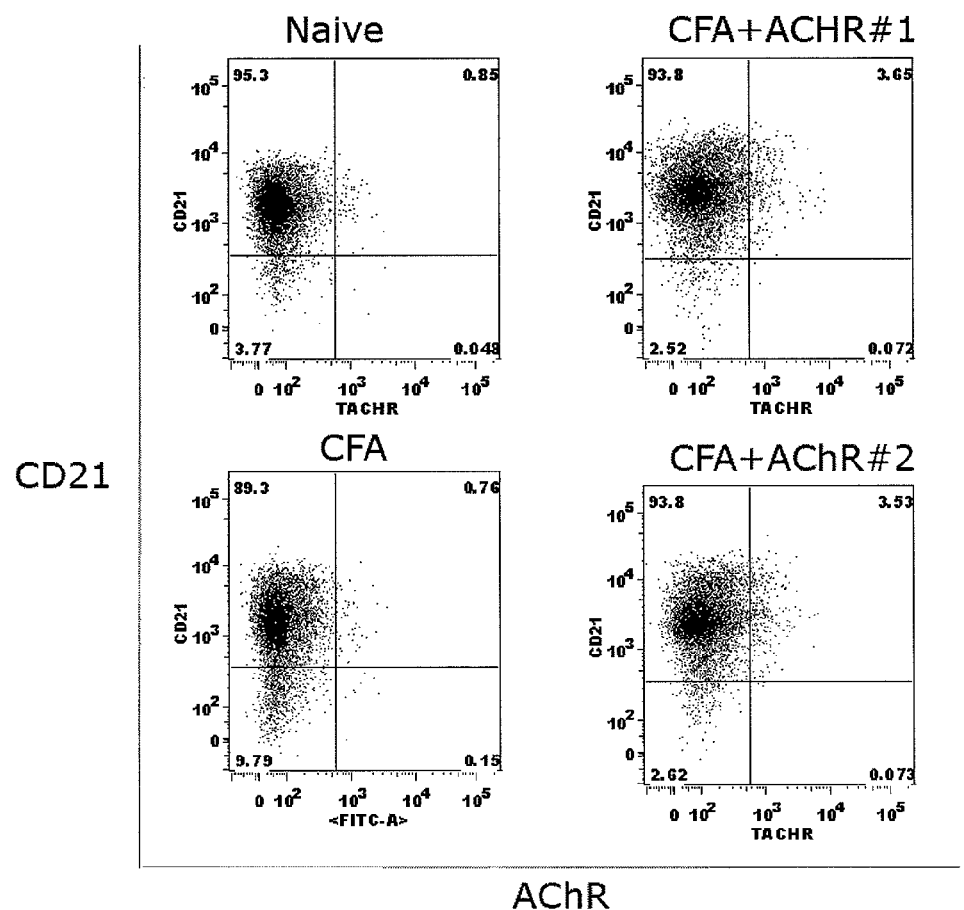
FIG. 2 Mature B cells (CD19+CD21) from CFA-AChR immunized mice have higher levels of Alexa-488 conjugated AChR+ splenocytes than naïve or CFA immunized mice.
Figure 3:
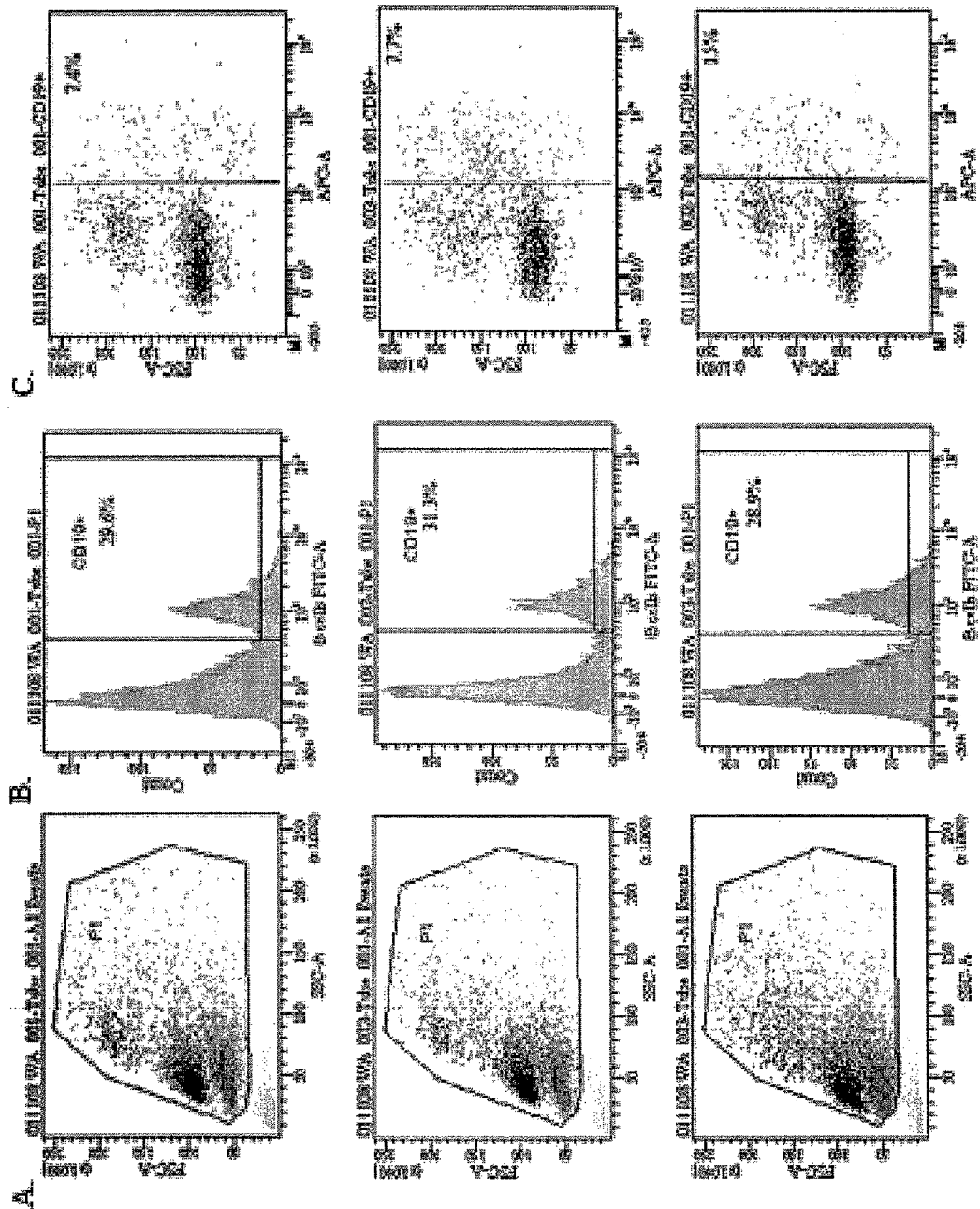
FIG. 3 Identifying AChR-specific B cells (CD19+) from lymph node of CFA-AChR immunized mice.

To identify AChR-specific B cells, mice were immunized with AChR to induce experimental autoimmune myasthenia gravis (EAMG) according to published methods (Wu et al., 1997). Mice were sacrificed four weeks post boost immunization with AChR in complete Freund's adjuvant. For control CFA immunized C57BL6 mice were used. Spleen cells, lymph node cells and blood mononuclear cells were labeled with APC-CD19, PE-CD21/35, and Alexa-488 AChR. First lymphocytes were gated on single cell suspension (FSC-A vs SSC-A, SSC-H vs SSC-W, and FSC-H vs FSC-W). Then cells were gated on B cells (APC-CD19+) and analyzed for binding of PE-CD21 (a mature B cell marker) and Alexa-488 (FITC-like) AChR. Splenocytes of mice immunized with AChR in CFA had more than double the amount of mature AChR+ B cells (CD19+CD21+AChR+) than unimmunized naïve mice and CFA immunized mice (FIG. 2). AChR in CFA immunized mice also had increased frequencies of AChR+ B cells in the lymph node compared to naïve mice. FIG. 3 shows AChR+ (APC) binding B cells (FITC-CD19+) frequencies in pooled lymph nodes in three separate mice with EAMG. AChR+ (APC like Alex 647-AChR) binding B cells are consistently elevated weeks post immunization and the size of a majority of these cells are large (FSC-A) indicating that these cells are activated (FIG. 3). In an independent experiment, Table 3 summarizes the mean percent CD19+ B cells which are AChR+ with SEM and N.

TABLE 3

Percent of B cells that were AChR+
in lymph node and spleen by flow cytometry

|  | Lymph Node | | | Spleen | | |
| --- | --- | --- | --- | --- | --- | --- |
|  | Mean | SEM | N | Mean | SEM | N |
| Naïve (pooled) | 5.6 | 0 | 1 | 6.4 | 0 | 1 |
| CFA + AChR | 10.38 | .61 | 7 | 11.36 | 1.5 | 7 |

Figure 4:
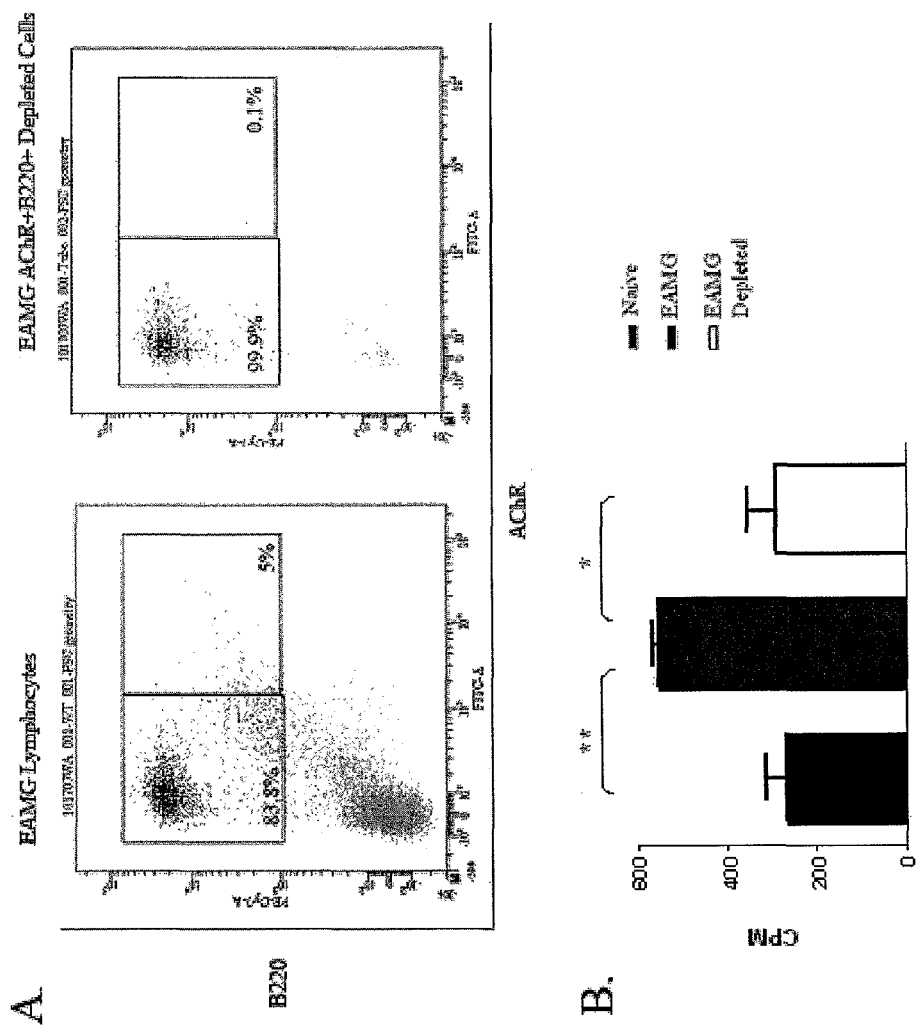
FIG. 4 Alexa-488 conjugated AChR+ cells are responsible for in vitro proliferative responses to AChR. (A) Double positive B cells (B220+AChR+) from CFA-AChR immunized mice were depleted by flow cytometry and (B) then stimulated in vitro with AChR.

To determine if B cells that bind AChR are specific for autoreactive immune responses in EAMG, B220+AChR− B cells were isolated from spleens of mice immunized with AChR in CFA. Next the inventors stimulated sorted B220+ AChR− (AChR+B cell depleted), total B220+ B cells from AChR in CFA immunized mice, and naïve mice in vitro with 1 µg/ml AChR (FIG. 4). AChR+B cell depleted cells had significantly reduced AChR-specific proliferation responses compared to total B220+ cells from EAMG mice. These results indicate that AChR binding B cells are specific for AChR.

There are many challenges identifying rare AChR-specific B cells. These results demonstrate that it is possible to identify the presence of AChR-specific B cells in lymphocyte populations. The frequency in total lymphocytes in EAMG animals is about 200 AChR+/100,000. Even for in vitro stimulation of purified AChR+B cells a minimum of 160 million B cells per animal would need to be sorted. However, two rounds of sorting would be required to achieve greater than 95% purity of AChR+ B cells. These results indicate that it is possible to characterize AChR-specific B cells in vivo.

Example 3

Figure 5:
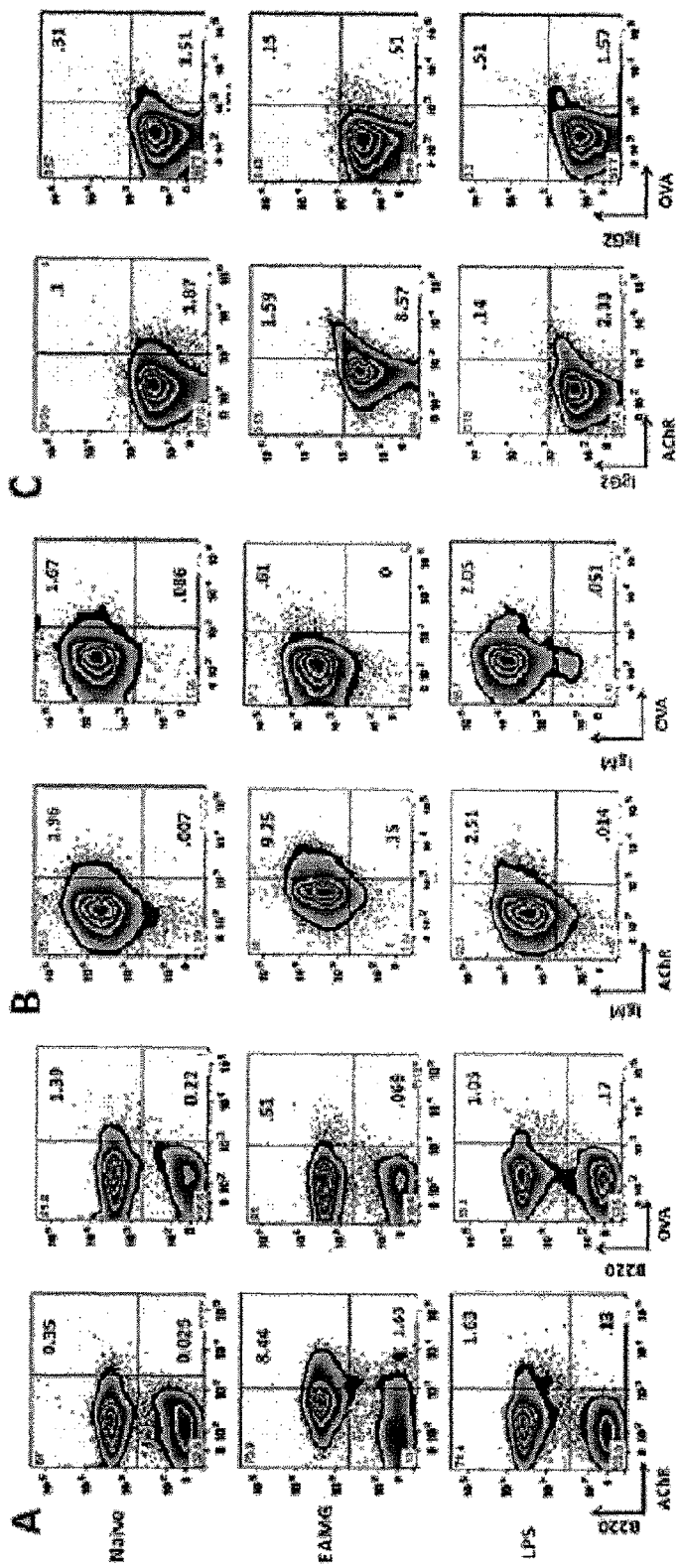
FIG. 5 The characterization of AChR-binding peripheral blood lymphocytes by flow cytometry. Representative flow cytometry analysis of peripheral blood lymphocytes from naïve, LPS-immunized or CFA+AChR-immunized (EAMG) mice, 75 to 80 days post primary immunization. Cells were first gated on lymphocytes and then analyzed for B220 expression and either AChR binding or OVA binding (A). Then lymphocytes were gated on B220+ cells to characterize IgM (B) or IgG2 (C) expression and either AChR binding or OVA binding. The numbers shown in bi-exponential plots indicate the relative percentage of cells in each quadrant. The experiment was repeated 5 times with similar results.
Figure 6:
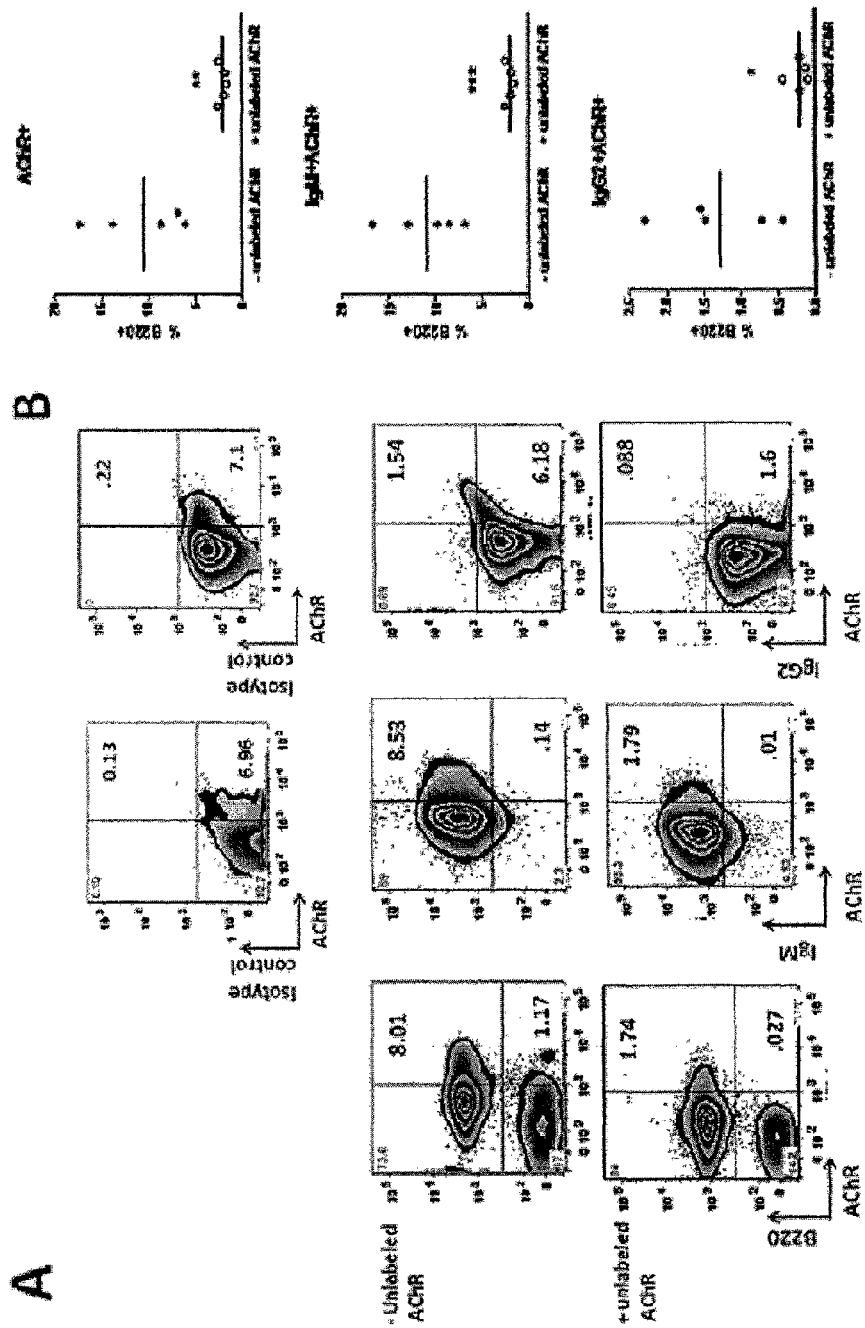
FIG. 6 Inhibition of Alexa fluor-AChR-binding to peripheral blood B cells with unlabeled AChR. Representative flow cytometry staining of peripheral blood lymphocytes with (+) or without (−) blocking by incubating cells with (+) unlabeled AChR prior to staining with Alexa fluor-AChR; anti-B220 and anti-IgM, anti-IgG2, or isotype controls (A). The numbers shown in bi-exponential plots indicate the relative percentage of cells in each quadrant. The mean percentage of B-cell, AChR-binding subsets with (+) or without (−) blocking with unlabeled AChR (B). Each circle represents the frequency of AChR-binding B cells after 3 immunizations with CFA+AChR from individual mice having EAMG (n=5). The bar indicates the mean frequency of AChR-binding B cells. The data shown are from one experiment that was repeated three times. *$P<0.05$, $P<0.01$, *$P<0.001$. t-test.

The Frequency of Acetylcholine Receptor-Specific B Cells Correlates with Experimental Myasthenia Gravis Severity Detection by flow cytometry of AChR-binding B cells among PBMCs of mice with EAM.G. Given the pathological significance of complement activation in MG, the inventors conducted a comparative flow cytometry study of AChR-binding B cells which express IgM or IgG2 in mice (Christadoss, 1988). To activate AChR-specific B lymphocytes, mice were immunized multiple times with AChR in CFA. The protocol was optimized by using whole blood drawn from mice with EAMG approximately 2 weeks post the third immunization with AChR emulsified in CFA; these results were then compared to those in naïve or LPS-immunized controls. Alexa fluor 647-AChR was used as a probe for potentially autoreactive AChR-specific B cells, while staining with Alexa fluor 647-OVA was used as a negative control. Shown in FIG. 5 is the typical staining patterns observed from blood stained with Alexa fluor-AChR, anti-B220, anti-IgM, and anti-IgG2. Alexa fluor-AChR preferentially bound to B220-expressing cells, which indicated to us that B cells are the main subset of peripheral lymphocytes capable of binding AChR (FIG. 5A). Furthermore, B220+ AChR-binding lymphocytes are most prominent in mice with EAMG. There is no significant increase in B220+ OVA-binding lymphocytes in mice with EAMG. These data suggest that the expansion of B220+ lymphocytes in mice with EAMG is specific to AChR-binding cells. To characterize these cells further, lymphocytes from the upper quadrants (B220+) were gated on and evaluated for expression of IgM or IgG2 and AChR-binding (FIGS. 1B and 1C). Although all mice had B220+IgM+ AChR-binding cells, these cells appeared at the highest frequencies in mice with EAMG (FIG. 5B). Conversely, only mice with EAMG had elevated frequencies of B220+IgG2+ AChR-binding cells (FIG. 5C). Background staining of blood lymphocytes with Alexa-OVA provided results showing the AChR-binding B cells are responsible for the increase in B cell frequencies. To confirm the specificity of this assay, inhibition of Alexa fluor 647-AChR binding to B cells was shown by incubating the cells with a 10-fold excess of unlabeled AChR prior to fluorescent labeling (FIG. 6). Alexa fluor-AChR staining of total B220+ cells, and IgM+ and IgG2+ B cells was significantly reduced by inhibition with unlabeled AChR.

Figure 7:
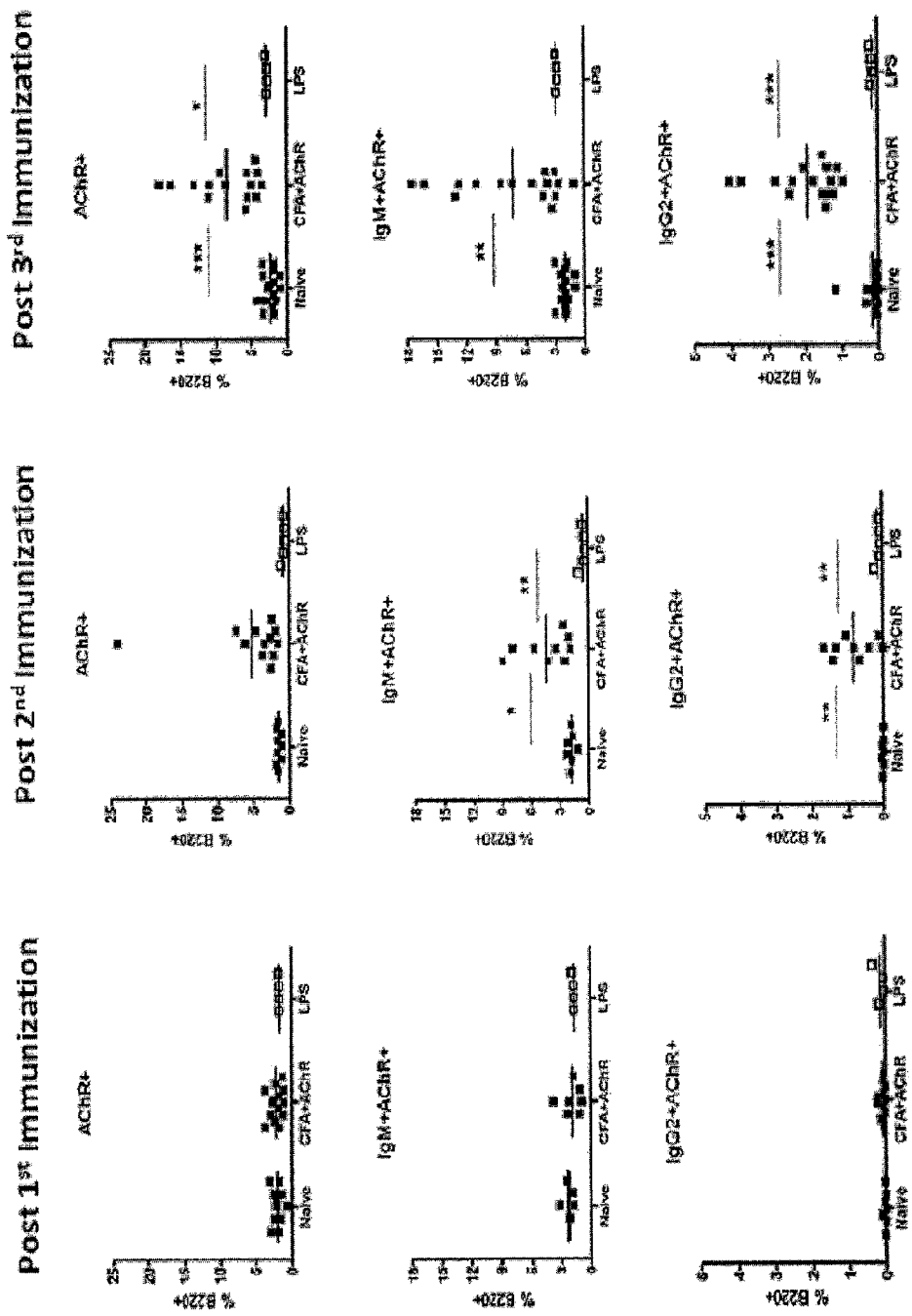
FIG. 7 The kinetics on the frequencies of AChR-binding B cells. Shown is the mean percentage of subsets of peripheral blood B cells which are AChR-binding from naïve, LPS-immunized or CFA+AChR-immunized (EAMG) mice. Cells were analyzed as shown in FIG. 1. Each square represents the frequency of the total AChR-binding B cells (top row), AChR-binding IgM+ B cells (middle row) or AChR-binding IgG2+ B cells (bottom row) from individual mice with EAMG after each immunization. Significant differences between populations were determined by ANOVA with Tukey's post hoc test and represented by a *$P<0.05$, $P<0.01$, and *$P<0.001$. Results shown are combined from multiple flow cytometry experiments with a total n=5-15 mice per group.

To determine the significance of the differences observed for AChR-binding B cell frequencies between mice with EAMG and controls, AChR-binding B cell frequency were evaluated at different time points following immunization with AChR in CFA. (FIG. 7). Using the analysis scheme described in FIG. 5, no significant differences in AChR-binding B cell frequencies were found at a week following the primary AChR immunization. After the second AChR immunization, the frequencies of AChR-binding peripheral blood B cells began to rise. Both B220+IgG2+ and B220+IgM+ AChR-binding B cell frequencies were significantly elevated compared to healthy and LPS immunized mice. After the third immunization, all subsets (B220+, B220+IgM+, B220+ IgG2+) of AChR-binding B cells analyzed were significantly elevated compared to findings with subsets in healthy naïve or LPS immunized mice (FIG. 7).

Figure 8:
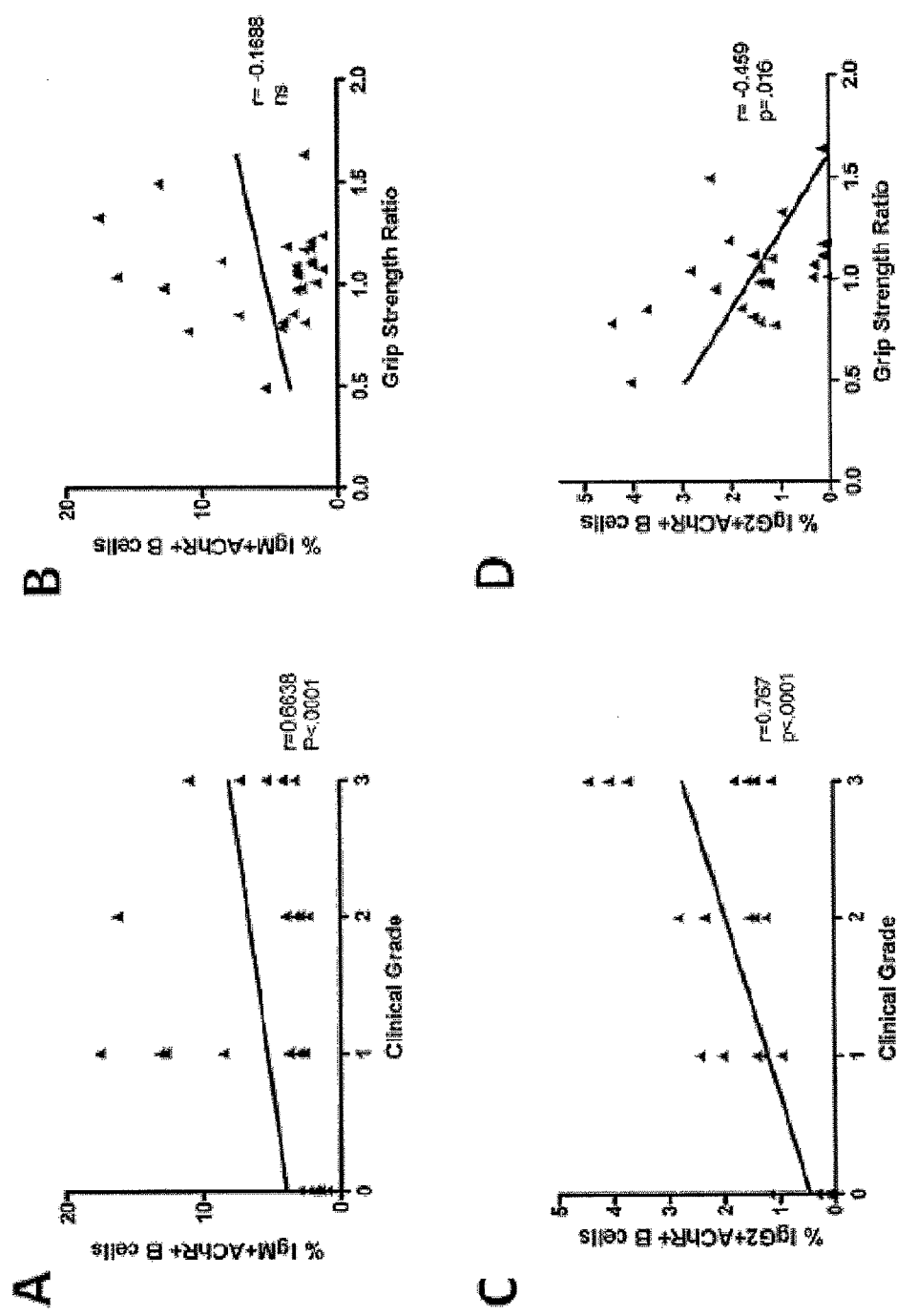
FIG. 8 Correlation between AChR-binding peripheral blood B cells and markers of disease severity. Each triangle represents the frequency of AChR-binding IgM+ (A&B) or IgG2+ (C&D) after 3 immunizations with CFA+AChR from individual mice with EAMG (clinical grades 1-3) and naïve mice (clinical grade 0) (n=5-7 per group). Clinical evaluation was completed at the time of blood draw (day 80). R is the Spearman coefficient between AChR-binding B-cell frequency and clinical grade (A&C) or grip strength loss represented by the grip strength ratio (B&D).

The appearance and frequency of peripheral blood AChR-specific B cells correlates with the severity of EAMG. Although the presence of serum antibodies to AChR indicates a possible diagnosis of MG, anti-AChR Ig concentrations are not reliable markers for disease severity (Christadoss et al., 1985; Krolick et al., 1994; Drachman et al., 1982). Clinical parameters of EAMG severity were used to determine whether the frequencies of peripheral blood AChR-specific B cells correlate with disease severity. The clinical grade of EAMG is a combination of several observed parameters of EAMG, such as posture, mobility, and muscle strength. Healthy unimmunized mice were assigned a clinical score of 0. A score of 1 is associated with no signs of EAMG prior to exercise or mild disease, a 2 indicates overall moderate symptoms of limb weakness, a score of 3 is associated with significant signs of muscle weakness without exercise and severe disease. After mice were immunized three times (day 75) with AChR in CFA, the frequencies of peripheral blood AChR-specific IgM+ and IgG2+ B cells were compared with the clinical grade of disease (FIG. 8). Earlier time points (days 7, 28, 42) were not evaluated due to the lack of animals with severe disease. IgM+ AChR-specific B cells in blood had a significant correlation with the clinical grade of EAMG ($r=0.6638$, $p<0.0001$, $n=5-7$ per grade) (FIG. 8A). IgG2 b+ AChR-specific B cells in blood also had a strong correlation with clinical grade ($r=0.767$, $p<0.0001$, $n=5-7$ per grade) (FIG. 8C).

Grip strength ratios are a more objective measurement of loss of muscle strength, described in detail in methods. A grip strength ratio>1 indicates an increase in strength over time, while a grip strength ratio≦1 indicates a loss of grip strength overtime. Mice which developed severe EAMG would have grip strength ratios≦1. IgM+ AChR binding B cells in blood had a no significant correlation ($r=-0.1688$, $p=0.3978$, $n=26$) with grip strength ratio (FIG. 8B). However, IgG2 b+ AChR-binding B cells in blood had a negative correlation ($r=-0.459$, $p<0.016$, $n=26$) with the grip strength ratio (FIG. 8D). Taken together, these results indicate that increased frequencies of peripheral blood AChR-specific B cells correspond to loss of limb muscle strength (grip strength ratio<1) and to higher clinical grades of disease. Furthermore, AChR-specific IgG2 expressing B cells is a good biomarker of disease severity.

Figure 9:
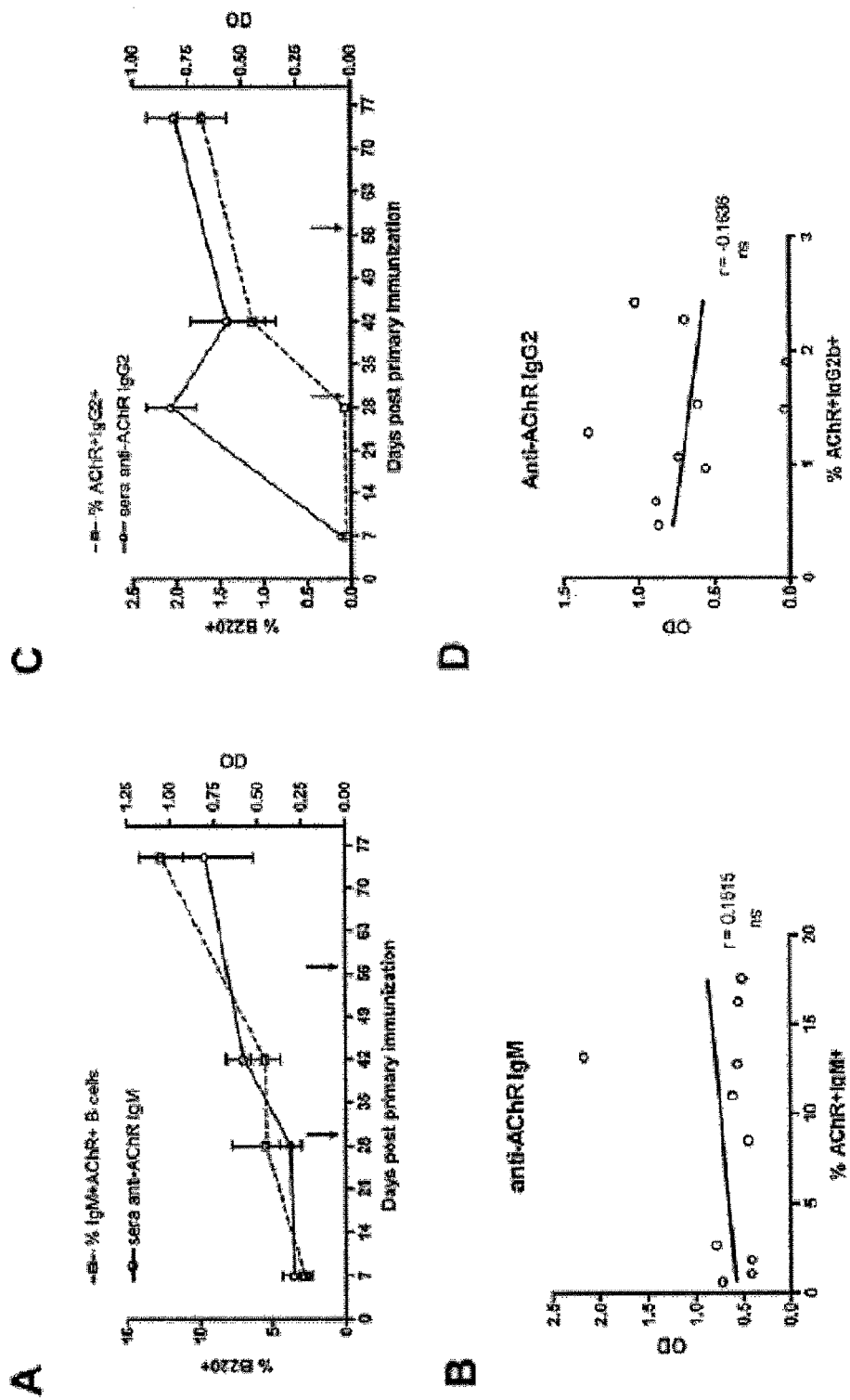
FIG. 9 Plasma concentration of secreted anti-AChR Igs does not correlate with the AChR-specific B-cell frequencies in mice with EAMG. Mean IgM (A) and IgG2 (C) expressing AChR-specific B-cell frequencies are shown by open squares with a broken line with SEM, and values are indicated on the left y-axis. Mean and SEM plasma anti-AChR IgM (A) and IgG2 (C) OD values determined by ELISA are shown by open circles with a solid line, and values are indicated on right axis. Spearman correlation between individual plasma anti-AChR IgM (B) or IgG2 (D) concentrations and the frequency of the AChR-binding B cells after day 42 post immunization. Each circle represents data from an individual mouse after each immunization with CFA and AChR. Black arrows indicate time of boost immunizations. Results shown are from one experiment with a total n=4-10 mice. Experiment was repeated with similar results. r, Spearman correlation coefficient; ns, not significant.

Plasma secreted anti AChR Igs do not correlate with the AChR-specific B cell frequencies in mice with EAMG. It has been previously demonstrated that sera or plasma anti-AChR Igs titers alone is not a reliable predictor of disease severity (Christadoss et al., 1985; Kroick et al., 1994; Lefvert et al., 1978). However, this new assay demonstrated that the frequencies of AChR-specific B cells is useful biomarker for disease severity. The association between AChR-specific B-cell frequencies and plasma anti-AChR concentrations was also evaluated (FIG. 9). Mice were immunized with CFA and AChR and bled at days 7, 28, 42, and 56. Plasma was separated from cells by centrifugation and analyzed for secreted anti-AChR Igs. Blood was then stained for AChR-binding B cells. Overall, the concentrations of anti-AChR Igs and frequencies of AChR-specific B cells tended to increase throughout the induction phase of EAMG (FIGS. 9A and 9C). However, at a time when animals have no disease symptoms (day 28), plasma anti-AChR IgG2 titers are significantly elevated. After boost immunization (day 42), mice began to show signs of disease, while plasma anti-AChR IgG2 titers started to decrease, the AChR-specific, IgG2-expressing B cells first began to appear in the peripheral blood. No significant correlation was found between individual mouse plasma anti-AChR level and specific peripheral B cell populations (FIGS. 9B and 9D).

Figure 10:
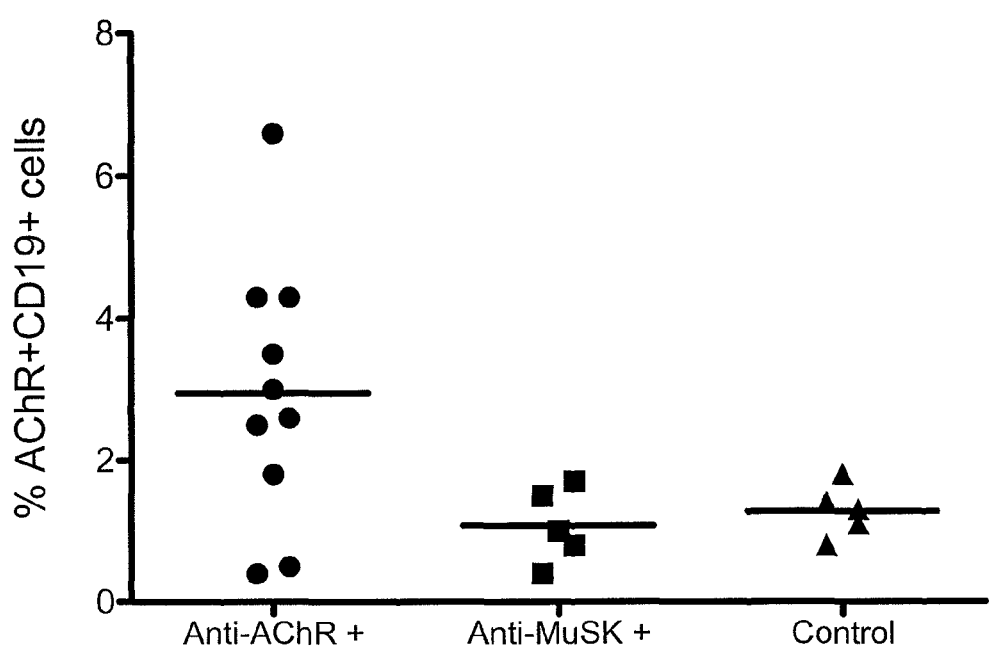
FIG. 10 Alexa-AxChR binding CD19+ B cells in patients with MG.

MG patients have higher frequency of AChR binding B cells. Peripheral blood from MG patients positive for anti-AChR or anti-MUSK antibody or healthy control were tested for their CD19+B cell binding to AChR by flow cytometry. Anti-AChR antibody positive MG patients, but not anti-MUSK+patients or healthy controls had higher frequency of B cells binding to AChR (FIG. 10).

Materials and Methods

Mice and induction of EAMG. C57BL/6 mice were purchased from the Jackson Laboratories (Bar Harbor, Me., USA). AChR extracted from Torpedo californica or from murine muscle tissue was purified on a neurotoxin affinity column, as previously described (Wu et al., 2001). EAMG was induced by emulsifying 100 μl CFA with 100 μl AChR (20 μg) in PBS. A separate group of mice were immunized with 100 μl of LPS (5 mg) emulsified in incomplete Freund's adjuvant for comparison. Both groups were anesthetized, and then immunized (200 μl/animal) with multiple s.c. injections in shoulders and foot pads. Mice were immunized 3 times, 28 days apart. All animals were housed in a barrier facility at the University of Texas Medical Branch and maintained according to the Institutional Animal Care and Use Committee guidelines.

Clinical Evaluation of EAMG. Evaluation of disease severity and muscle weakness was performed immediately prior to blood draw and at 2 weeks after each immunization and measured as follows: Grade 0, normal mobility, posture and grip strength; Grade 1, hunchback posture, restricted mobility and decreased muscle grip strength after paw grip exercises; Grade 2, without exercise, observed hunchback posture, restricted mobility and decreased muscle grip strength; Grade 3, dehydrated and moribund with grade 2 weakness, death, or euthanasia due to paralysis. Mice were exercised by 30 paw grips on the cage top grid. Following exercise, and grip strength was measured by a dynamometer (Chatillon Digital Force Gauge, DFIS. 2, Columbus Instruments, Columbus, Ohio). The grip strength ratio for each mouse at each time point was determined by dividing the average grip strength post immunization by the average grip strength prior to immunization. A grip strength ratio>1 indicates an increase in strength over time, while a grip strength ratio≦1 indicates a loss of grip strength overtime.

Conjugation of Alexa Fluor 647 to AChR. AChR was purified from torpedo californica electric organs (Aquatic Research Consultants, CA) according to published methods (Wu et al., 2001). AChR was concentrated by centrifugation with CentriconYM (10,000 molecular weight) centrifugal filters (Millipore, Mass.). AChR was then dialyzed in PBS by using Spectra/Por dialysis tubing (12-14,000 molecular weight). AChR was labeled with Alexa Fluor 647 Protein Labeling Kit (Invitrogen) according to the manufacturer's instructions.

Blood collection, Flow Cytometry, and ELISA Blood was collected from the tail vein into $K_2$EDTA microtubes at 7 days after primary immunization and at 2 weeks following the $2^{nd}$ and $3^{rd}$ immunization. In keeping with previously published ELISA protocols, blood was centrifuged at 500 g for 15 min, and plasma removed for analysis of secreted anti-AChR-Igs (Yang et al., 2005). Blood was then treated with BD Pharm Lyse Buffer. Fcγ receptors were blocked with anti-CD16/32 Ab (Ab 93, eBioscience). Fifty μl of whole blood was stained for surface markers with Alexa fluor 647-AChR or Alexa fluor 647-Ovalbumin (Ova) and PE-Cy7-anti B220 (RA3-6B2), then fixed and permeabilized by using a Cytoperm/Cytofix kit (BD Biosciences) according to standard protocols for flow cytometry. Cells were then stained with anti-IgG2 b (R12-3) and anti-IgM (eB121-15F9) Abs or isotype controls. Cell populations were determined using a BD FACS Canto and FlowJo v 7.2 (Tree Star).

Statistics. Cell phenotype was analyzed using an ANOVA with a two-tail p value. Correlation of cell frequencies to clinical grade, grip strength ratio, and plasma secreted anti-AChR Igs were determined by a Spearman correlation with a two-tail p value. The linear regression model was used to fit data.

REFERENCES

The following references, to the extent that they provide exemplary procedural or other details supplementary to those set forth herein, are specifically incorporated herein by reference.

U.S. Pat. No. 4,554,101
U.S. Pat. No. 4,879,236
U.S. Pat. No. 5,871,986
A Practical Approach, Athert on & Sheppard (Eds.), IRL Press, Oxford, England, 1989.
Aharonov et al., *Lancet.*, 2(7930):340-2, 1975.
Balass et al., *Proc. Natl. Acad. Sci. USA*, 90(22):10638-10642, 1993.
Barany and Merrifield, In: *The Peptides*, Gross and Meienhofer (Eds.), Academic Press, NY, 1-284, 1979.
Bartfeld and Fuchs, *Proc. Natl. Acad. Sci. USA*, 75(8):4006-4010, 1978.
Beeson et al., *EMBO J.*, 9(7):2101-2106, 1990.
Brinkley, *Bioconjugate Chem.*, 3(1):2-13, 1992.
Changeux et al., *Science*, 225(4668):1335-1345, 1984.
Chemical Approaches to the Synthesis of Peptides and Proteins, Williams et al. (Eds.), CRC Press, Boca Raton Fla., 1997.
Christadoss et al., *J. Neuroimmunol.*, 8:29-41, 1985.
Christadoss, *J. Immunol.*, 140:2589-2592, 1988.
Creighton, Proteins; Structures and Molecular Principles, W.H. Freeman and Co., NY, 1983
De Leon-Rodriguez et al., *Chem. Eur. J.*, 10:1149-1155, 2004.
Drachman et al., *N. Engl. J. Med.*, 307:769-775, 1982.
Drachman, *N. Engl. J. Med.*, 330(25):1797-1810, 1994.
Garman, In: *Non-Radioactive Labelling: A Practical Approach*, Academic Press, London, 1997.
Gene Expression Technology, Method in Enzymology, Genetics and Molecular Biology, Method in Enzymology, Guthrie & Fink (Eds.), Academic Press, San Diego, Calif., 1991.
Glazer et al., In: *Chemical Modification of Proteins*. Laboratory Techniques in Biochemistry and Molecular Biology, Work and Work (Eds.), American Elsevier Pub. Co., NY, 1975.
Haugland, In: *Molecular Probes Handbook of Fluorescent Probes and Research Chemicals*, Molecular Probes, Inc., 2003.
Hitzeman et al., *J. Bio. Chem.*, 255:12073-12080, 1990.
Karlin, *J. Theor. Biol.*, 87(1):33-54, 1980.
Krolick et al., *Adv. Neuroimmunol.*, 4:475-493, 1994.
Kyte and Doolittle, *J. Mol. Biol.*, 157(1):105-132, 1982.
Lefvert et al., *J. Neurol. Neurosurg. Psychiatry*, 41:394-403, 1978.
Lewis et al., *Bioconjugate Chem.*, 12:320-324, 2001.
Li et al., *Bioconjugate Chem.*, 13:110-115, 2002.
Loutrari et al., *Eur. J. Immunol.*, 22(9):2449-2452, 1992.
Lundblad and Noyes, In: *Chemical Reagents for Protein Modification*, Vols. I and II, CRC Press, NY, 1984.
Maniatis, et al., *Molecular Cloning*, A Laboratory Manual, Cold Spring Harbor Press, Cold Spring Harbor, N.Y., 1982.
Means and Feeney, *Bioconjugate Chem.*, 1(1):2-12, 1990.
Merrifield, *Science*, 232(4748):341-347, 1986.
Mier et al., *Bioconjugate Chem.*, 16:240-237, 2005.
Noda et al., *Nature*, 305(5937):818-823, 1983.
Patrick and Lindstrom, *Science*, 180:871-872, 1973.
Pfleiderer, In: *Chemical Modification of Proteins*, Modern Methods in Protein Chemistry, Tschesche (Ed.), Walter DeGryter, Berlin and NY, 1985.
Sambrook et al., *Molecular Cloning*: A Laboratory Manual, Cold Spring Harbor Press, NY, 2nd Ed., 1998
Sambrook et al., *Molecular Cloning*: A Laboratory Manual, Cold Spring Harbor Press, NY, $3^{rd}$ Ed., 2000.
Schoepfer et al., *FEES Lett.*, 226(2):235-240, 1988.
Shenoy et al., *Clin. Immunol. Immunopathol.*, 66(3):230-238, 1993.
Souroujon et al., *Ann. NY Acad. Sci.*, 681:332-334, 1993.
Souroujon et al., *Immunol. Lett.*, 34(1):19-25, 1992.
Stewart and Young, In: *Solid Phase Peptide Synthesis*, 2d. ed., Pierce Chemical Co., 1984.
Structures and Molecular Principles, W.H. Freeman and Co., NY, 1983.
Tam et al., *J. Am. Chem. Soc.*, 105:6442, 1983.
Tzartos and Lindstrom, *Proc. Natl. Acad. Sci. USA*, 77(2):755-759, 1980.
Tzartos et al., *Neuroimmunol.*, 15(2):185-194, 1987.
Wong, *Chemistry of Protein Conjugation and Cross-Linking*, CRC Press, Boca Raton, Fla., 1991.
Wu et al., *Curr. Protoc. Immunol.*, 15:Unit 15-18, 2001.
Wu, et al., In: *Experimental Autoimmune Myasthenia Gravis in the Mouse. Current Protocols in Immunology*. John Wiley & Sons, Inc, Chap. 15.8, 1997.

The invention claimed is:

1. A method for evaluating a patient for or with Myasthenia Gravis comprising contacting B cells in a sample from the patient with an acetylcholine receptor (AChR) conjugate comprising a main immunogenic region (MIR) of acetylcholine receptor alpha subunit coupled to a detectable moiety; and measuring the level of AChR conjugate-binding B cells.

2. The method of claim 1, wherein AChR conjugate binding is evaluated with respect to a reference or standard.

3. The method of claim 1, wherein the sample is a blood sample.

4. The method of claim 1, wherein the AChR conjugate comprises a fluorophore.

5. The method of claim 4, wherein the fluorophore is an Alexa fluorophore.

6. The method of claim 5, wherein the Alexa fluorophore is Alexa-488 or Alexa-647.

7. The method of claim 1, wherein measuring the level of AChR binding B cells is by flow cytometry.

8. The method of claim 1, further comprising contacting the sample with a B cell marker binding agent.

9. The method of claim 8, wherein the B cell marker binding agent is an antibody.

10. The method of claim 9, wherein the marker is a cell surface molecule.

11. The method of claim 9, wherein the antibody binds IgG, CD19, CD21, CD45R, CD20, CD22, CD23, or CD81.

12. The method of claim 1, further comprising administering a treatment for myasthenia gravis.

13. The method of claim 1, wherein the acetylcholine receptor (AChR) conjugate comprises an acetylcholine receptor alpha subunit coupled to a detectable moiety.

14. The method of claim 1, wherein the acetylcholine receptor (AChR) conjugate comprises an acetylcholine receptor coupled to a detectable moiety.

15. A method of evaluating a patient for or with Myasthenia Gravis comprising the steps of:
    (i) contacting a sample comprising B cells from the patient with a AChR conjugate that binds a B cell associated with Myasthenia Gravis;
    (ii) determining a level of conjugate binding B cells in the sample; and
    (iii) comparing the level of conjugate binding B cells with a reference or standard.

16. The method of claim 15, wherein the acetylcholine receptor (AChR) conjugate comprises an acetylcholine receptor alpha subunit coupled to a detectable moiety.

17. The method of claim 15, wherein the acetylcholine receptor (AChR) conjugate comprises an acetylcholine receptor coupled to a detectable moiety.

* * * * *